(12) United States Patent
Garg et al.

(10) Patent No.: US 10,738,292 B2
(45) Date of Patent: Aug. 11, 2020

(54) CELLULASE DERIVED FROM METAGENOMICS

(71) Applicant: Council of Scientific & Industrial Research, New Delhi (IN)

(72) Inventors: Roma Garg, Chandigarh (IN); Vijaya Brahma, Chandigarh (IN); Lata Verma, Chandigarh (IN); Girish Sahni, Chandigarh (IN)

(73) Assignee: Council of Scientific & Industrial Research, New Delhi (IN)

( * ) Notice: Subject to any disclaimer, the term of this patent is extended or adjusted under 35 U.S.C. 154(b) by 27 days.

(21) Appl. No.: 15/775,652

(22) PCT Filed: Nov. 11, 2016

(86) PCT No.: PCT/IN2016/050395
§ 371 (c)(1),
(2) Date: May 11, 2018

(87) PCT Pub. No.: WO2017/081705
PCT Pub. Date: May 18, 2017

(65) Prior Publication Data
US 2018/0371442 A1   Dec. 27, 2018

(30) Foreign Application Priority Data
Nov. 12, 2015 (IN) .......................... 3690/DEL/2015

(51) Int. Cl.
*C12N 1/20* (2006.01)
*C12N 9/42* (2006.01)
*C12N 15/10* (2006.01)

(52) U.S. Cl.
CPC ....... *C12N 9/2437* (2013.01); *C12N 15/1093* (2013.01); *C12Y 302/01004* (2013.01)

(58) Field of Classification Search
CPC .................. C12N 9/2437; C12Y 302/01004
USPC ....................................................... 435/209
See application file for complete search history.

(56) References Cited

FOREIGN PATENT DOCUMENTS

| EP | 1612267 A1 | 1/2006 |
|----|-----------|--------|
| WO | 2006003175 A1 | 1/2006 |

OTHER PUBLICATIONS

Aubert, J. et al., "Biochemistry and genetics of cellulose degradation", 1988, Academic Press.
Bhat, M. "Cellulases and related enzymes in biotechnology", 2000, Biotechnology advances 18, pp. 355-383.
Choi, N. et al., "Multiple-layer substrate zymography for detection of several enzymes in a single sodium dodecyl sulfate gel", 2009, Analytical biochemistry 386, pp. 121-122.
Daniel, R., "The metagenomics of soil" 2005, Nat Rev Microbiol 3, pp. 470-478.
Handelsman, J., "Metagenomics: application of genomics to uncultured microorganisms", 2004, Microbiol Mol Biol Rev 68, pp. 669-685.
Kanokratana, P. et al., "Identification of glycosyl hydrolases from a metagenomic library of microflora in sugarcane bagasse collection site and their cooperative action on cellulose degradation", 2014, Journal of bioscience and bioengineering.
Ko, K. et al., "A novel multifunctional cellulolytic enzyme screened from metagenomic resources representing ruminal bacteria", 2013, Biochemical and biophysical research communications 441, pp. 567-572.
Laemmli, U.K., "Cleavage of structural proteins during the assembly of the head of bacteriophage T4", 1970, Nature 227, pp. 680-685.
Lombard, V. et al., "The carbohydrate-active enzymes database (CAZy) in 2013". Nucleic Acids 2014 Res 42, pp. D490-D495.
Lynd, L.R. et al., "Microbial cellulose utilization: fundamentals and biotechnology. Microbiology and molecular biology reviews", 2002, 66, pp. 506-577.
Miller, G.L., "Use of dinitrosalicylic acid reagent for determination of reducing sugar", 1959, Analytical chemistry 31, pp. 426-428.
Okano, H. et al., "Structure and stability of metagenome-derived glycoside hydrolase family 12 cellulase (LC-Ce1A) a homolog of Cel12A from Rhodothermus marinus", 2014, FEBS Open Bio 4, pp. 936-946.
Petersen, T.N. et al., "SignalP 4.0: discriminating signal peptides from transmembrane regions", 2011, Nat Methods 8, pp. 785-786.
Sambrook, J., and Russell, D.W. "Molecular Cloning: A Laboratory Manual", 2001, (Cold Spring Harbor Laboratory Press).
Teather, R.M. et al., "Use of Congo red-polysaccharide interactions in 25 enumeration and characterization of cellulolytic bacteria from the bovine rumen", 1982, Appl Environ Microbiol 43, pp. 777-780.
Xiao, Z. et al., "Microplate-based carboxymethylcellulose assay for endoglucanase activity", 2005, Anal Biochem 342, pp. 176-178.
Xing, M et al., "Application of metagenomic 30 techniques in mining enzymes from microbial communities for biofuel synthesis", 2012, Biotechnology advances 30, pp. 920-929.

(Continued)

*Primary Examiner* — Tekchand Saidha
(74) *Attorney, Agent, or Firm* — Dinsmore & Shohl, LLP

(57) ABSTRACT

The present invention relates to a novel endoglucanase gene (GH5 family) from the soil metagenome. More specifically, this invention provides a recombinant plasmid and the recombinant hosts for the expression of novel gene sequence having cellulase activity. The cellulase in the invention has high specific activity towards β-1,4 linkages in substrates such as carboxy-methyl cellulose and barley-β-glucan etc. This novel cellulase can have many industrial applications eg. food and feed industry, detergent, textile and biofuel industry etc.

7 Claims, 12 Drawing Sheets
Specification includes a Sequence Listing.

(56) References Cited

OTHER PUBLICATIONS

Zengler, K. et al., "Cultivating the uncultured", 2002, Proc Natl Acad Sci U S A, 99, pp. 15681-15686.
Xin Li et al., "Characterization of a halostable endoglucanase with organic solvent-tolerant property from *Haloarcula* sp. G10", 2013, International Journal of Biological Macromolecules, vol. 62, pp. 101-106.
Voget S. et al., "Characterization of a metagenome-derived halotolerant cellulase", 2006, Journal of Biotechnology, vol. 126, No. 1, pp. 26-36.
Ilmberger N. et al., "Metagenomic cellulases highly tolerant towards the presence of ionic liquids—linking thermostability and halotolerance", 2012, Applied Microbiology and Biotechnology, vol. 95, No. 1, pp. 135-146.
Roma Garg et al., "Biochemical and structural characterization of a novel halotolerant cellulase from soil metagenome", 2016, Scientific Reports, vol. 6, No. 1, pp. 1-15.
European Nucleotide Archive, uncultured bacterium cellulase GH5, May 16, 2016, XP002769883, retrieved from EBI Accession No. EMBL:AND76761, pp. 1-2.
UniProt, "Full=Cellulase GH5", Sep. 7, 2016, XP002769884, retrieved from EBI accession No. UniProt:A0A172PZJ4, p. 1.
UniProt, "Full=Cellulase (Glycosyl hydrolase family 5)", Mar. 23, 2010, XP002769885, retrieved from EBI accession No. UniProt:D3HV64, p. 1.
International Search Report and Written Opinion completed May 8, 2017, pertaining to PCT/IN2016/050395, filed Nov. 11, 2016.

SEQUENCE LISTING

```
<160> NUMBER OF SEQ ID NOS: 45

<210> SEQ ID NO 1
<211> LENGTH: 1017
<212> TYPE: DNA
<213> ORGANISM: unknown
<220> FEATURE:
<223> OTHER INFORMATION: Soil metagenome derived nucleotide sequence

<400> SEQUENCE: 1
atgaagaaaa actcaatcat tctcacactg gttcttttg ttattgttgc tttgtcctgt      60
accggcagca gtaaaaaaac ggaaaacaac aggaaaacgg actaccgttc catcgtagcg     120
cagaacggcc gtttacaggt gatcggcaca caattgagca atgaaaagg cgaacccgtc     180 gttttacggg gagccagcct cggatggcac aacctctggc cccgcttcta taacaagaac     240
gcggtgcaat ggctggccga cgattggaaa tgcacggtcg tcagggctgc aatgggcttg     300
gaaattgaag acaactaccg ggaaaatccc gaatttgcct tacagtgcat caccctgtc     360 atcgaatcgg ctattgaaaa cggaatctat gtgattatcg acttccacgc acacaacaaa    420
tacaccgaag aagccaaaac attctttgcc gggatggccg aaaaatacgg ggaatatccg     480
aacgtgatct atgaaatctg gaacgaaccc gattatttcg aatgggaaga agtaaaaacc    540
tattcggaag aagtgatcgc cgtcatccgc gcgatcgacc ccgacaatat tatattggtc    600
ggcagccccc attgggacca ggacctgcat ctggtagccg aagacccgat ccgggatgta    660
agcaacatca tgtacaccat gcatttttac gccgcgaccc acgaggcctg gctgcgtgac    720
cggaccgacg aggcgattgc caaggaatt cccgttttcg tatcggagtg cggcggctcg    780
gaagccaatg gcgacggacg gttaggcata gaagaatgga aaacctacgt cgattggatg     840
gagagtcgga aaataagctg gtgtgccctgg tccgttttcc acaagaacga aacctgctcc    900
atgctgctcc cccgcgcctc tgccgatggc aactggacgg aagacctgct caagccttgg    960
ggaaaactga cgcgtaattc tatccggaac gcgaatgatg aaaacccgga tatctga      1017

<210> SEQ ID NO 2
<211> LENGTH: 338
<212> TYPE: PRT
<213> ORGANISM: unknown
<220> FEATURE:
<223> OTHER INFORMATION: Polypeptide sequence of the cellulase derived
      from soil metagenome

<400> SEQUENCE: 2

Met Lys Lys Asn Ser Ile Ile Leu Thr Leu Val Leu Phe Val Ile Val
1               5                   10                  15

Ala Leu Ser Cys Thr Gly Ser Ser Lys Lys Thr Glu Asn Asn Arg Lys
            20                  25                  30

Thr Asp Tyr Arg Ser Ile Val Ala Gln Asn Gly Arg Leu Gln Val Ile
        35                  40                  45

Gly Thr Gln Leu Ser Asn Glu Lys Gly Glu Pro Val Val Leu Arg Gly
    50                  55                  60
```

```
Ala Ser Leu Gly Trp His Asn Leu Trp Pro Arg Phe Tyr Asn Lys Asn
 65                  70                  75                  80

Ala Val Gln Trp Leu Ala Asp Asp Trp Lys Cys Thr Val Val Arg Ala
                 85                  90                  95

Ala Met Gly Leu Glu Ile Glu Asp Asn Tyr Arg Glu Asn Pro Glu Phe
            100                 105                 110

Ala Leu Gln Cys Ile Thr Pro Val Ile Glu Ser Ala Ile Glu Asn Gly
            115                 120                 125

Ile Tyr Val Ile Ile Asp Phe His Ala His Asn Lys Tyr Thr Glu Glu
130                 135                 140

Ala Lys Thr Phe Phe Ala Gly Met Ala Glu Lys Tyr Gly Glu Tyr Pro
145                 150                 155                 160

Asn Val Ile Tyr Glu Ile Trp Asn Glu Pro Asp Tyr Phe Glu Trp Glu
                165                 170                 175

Glu Val Lys Thr Tyr Ser Glu Val Ile Ala Val Ile Arg Ala Ile
            180                 185                 190

Asp Pro Asp Asn Ile Ile Leu Val Gly Ser Pro His Trp Asp Gln Asp
            195                 200                 205

Leu His Leu Val Ala Glu Asp Pro Ile Arg Asp Val Ser Asn Ile Met
210                 215                 220

Tyr Thr Met His Phe Tyr Ala Ala Thr His Glu Ala Trp Leu Arg Asp
225                 230                 235                 240

Arg Thr Asp Glu Ala Ile Ala Lys Gly Ile Pro Val Phe Val Ser Glu
                245                 250                 255

Cys Gly Gly Ser Glu Ala Asn Gly Asp Gly Arg Leu Gly Ile Glu Glu
            260                 265                 270

Trp Lys Thr Tyr Val Asp Trp Met Glu Ser Arg Lys Ile Ser Trp Val
            275                 280                 285

Ala Trp Ser Val Ser Asp Lys Asn Glu Thr Cys Ser Met Leu Leu Pro
290                 295                 300

Arg Ala Ser Ala Asp Gly Asn Trp Thr Glu Asp Leu Leu Lys Pro Trp
305                 310                 315                 320

Gly Lys Leu Thr Arg Asn Ser Ile Arg Asn Ala Asn Asp Glu Asn Pro
                325                 330                 335

Asp Ile
```

<210> SEQ ID NO 3
<211> LENGTH: 936
<212> TYPE: DNA
<213> ORGANISM: Artificial sequence
<220> FEATURE:
<223> OTHER INFORMATION: Sequence derived from soil metagenome,
      particularly nucleotide sequence of the gene after truncating the
      upstream hydrophobic patch

<400> SEQUENCE: 3

```
gaaaacaaca ggaaaacgga ctaccgttcc atcgtagcgc agaacggccg tttacaggtg      60
atcggcacac aattgagcaa tgaaaaaggc gaacccgtcg ttttacgggg agccagcctc     120
ggatggcaca acctctggcc ccgcttctat aacaagaacg cggtgcaatg gctggccgac     180
gattggaaat gcacggtcgt cagggctgca atgggcttgg aaattgaaga caactaccgg     240
gaaaatcccg aatttgcctt acagtgcatc acccctgtca tcgaatcggc tattgaaaac     300
ggaatctatg tgattatcga cttccacgca cacaacaaat acaccgaaga agccaaaaca     360
ttctttgccg ggatggccga aaaatacggg gaatatccga acgtgatcta tgaaatctgg     420
```

-continued

```
aacgaacccg attatttcga atgggaagaa gtaaaaacct attcggaaga agtgatcgcc        480
gtcatccgcg cgatcgaccc cgacaatatt atattggtcg gcagcccca ttgggaccag         540 gacctgcatc tggtagccga agacccgatc cgggatgtaa gcaacatcat gtacaccatg        600 cattttacg ccgcgaccca cgaggcctgg ctgcgtgacc ggaccgacga ggcgattgcc         660
aaaggaattc ccgttttcgt atcggagtgc ggcggctcgg aagccaatgg cgacggacgg        720
ttaggcatag aagaatggaa aacctacgtc gattggatgg agagtcggaa ataagctgg         780 gtggcctggt ccgtttccga caagaacgaa acctgctcca tgctgctccc ccgcgcctct       840
gccgatggca actggacgga agacctgctc aagccttggg gaaaactgac gcgtaattct       900
atccggaacg cgaatgatga aaacccggat atctga                                  936
```

<210> SEQ ID NO 4
<211> LENGTH: 311
<212> TYPE: PRT
<213> ORGANISM: Artificial sequence
<220> FEATURE:
<223> OTHER INFORMATION: Sequence derived from soil metagenome,
      particularly polypeptide sequence of the gene after truncating the
      upstream hydrophobic patch

<400> SEQUENCE: 4

```
Glu Asn Asn Arg Lys Thr Asp Tyr Arg Ser Ile Val Ala Gln Asn Gly
1               5                   10                  15

Arg Leu Gln Val Ile Gly Thr Gln Leu Ser Asn Glu Lys Gly Glu Pro
            20                  25                  30

Val Val Leu Arg Gly Ala Ser Leu Gly Trp His Asn Leu Trp Pro Arg
        35                  40                  45

Phe Tyr Asn Lys Asn Ala Val Gln Trp Leu Ala Asp Asp Trp Lys Cys
    50                  55                  60

Thr Val Val Arg Ala Ala Met Gly Leu Glu Ile Glu Asp Asn Tyr Arg
65                  70                  75                  80

Glu Asn Pro Glu Phe Ala Leu Gln Cys Ile Thr Pro Val Ile Glu Ser
                85                  90                  95

Ala Ile Glu Asn Gly Ile Tyr Val Ile Ile Asp Phe His Ala His Asn
            100                 105                 110

Lys Tyr Thr Glu Glu Ala Lys Thr Phe Phe Ala Gly Met Ala Glu Lys
        115                 120                 125

Tyr Gly Glu Tyr Pro Asn Val Ile Tyr Glu Ile Trp Asn Glu Pro Asp
    130                 135                 140

Tyr Phe Glu Trp Glu Glu Val Lys Thr Tyr Ser Glu Glu Val Ile Ala
145                 150                 155                 160

Val Ile Arg Ala Ile Asp Pro Asp Asn Ile Ile Leu Val Gly Ser Pro
                165                 170                 175

His Trp Asp Gln Asp Leu His Leu Val Ala Glu Asp Pro Ile Arg Asp
            180                 185                 190

Val Ser Asn Ile Met Tyr Thr Met His Phe Tyr Ala Ala Thr His Glu
        195                 200                 205

Ala Trp Leu Arg Asp Arg Thr Asp Glu Ala Ile Ala Lys Gly Ile Pro
    210                 215                 220

Val Phe Val Ser Glu Cys Gly Gly Ser Glu Ala Asn Gly Asp Gly Arg
225                 230                 235                 240

Leu Gly Ile Glu Glu Trp Lys Thr Tyr Val Asp Trp Met Glu Ser Arg
                245                 250                 255

Lys Ile Ser Trp Val Ala Trp Ser Val Ser Asp Lys Asn Glu Thr Cys
```

```
                        260                 265                 270
Ser Met Leu Leu Pro Arg Ala Ser Ala Asp Gly Asn Trp Thr Glu Asp
            275                 280                 285

Leu Leu Lys Pro Trp Gly Lys Leu Thr Arg Asn Ser Ile Arg Asn Ala
            290                 295                 300

Asn Asp Glu Asn Pro Asp Ile
305                 310

<210> SEQ ID NO 5
<211> LENGTH: 311
<212> TYPE: PRT
<213> ORGANISM: Artificial sequence
<220> FEATURE:
<223> OTHER INFORMATION: Sequence representing single alanine
      substitution made on SEQ ID NO 4 wherein cysteine 64 is replaced
      by alanine

<400> SEQUENCE: 5

Glu Asn Asn Arg Lys Thr Asp Tyr Arg Ser Ile Val Ala Gln Asn Gly
1               5                   10                  15

Arg Leu Gln Val Ile Gly Thr Gln Leu Ser Asn Glu Lys Gly Glu Pro
            20                  25                  30

Val Val Leu Arg Gly Ala Ser Leu Gly Trp His Asn Leu Trp Pro Arg
            35                  40                  45

Phe Tyr Asn Lys Asn Ala Val Gln Trp Leu Ala Asp Asp Trp Lys Ala
50                  55                  60

Thr Val Val Arg Ala Ala Met Gly Leu Glu Ile Glu Asp Asn Tyr Arg
65                  70                  75                  80

Glu Asn Pro Glu Phe Ala Leu Gln Cys Ile Thr Pro Val Ile Glu Ser
                85                  90                  95

Ala Ile Glu Asn Gly Ile Tyr Val Ile Asp Phe His Ala His Asn
            100                 105                 110

Lys Tyr Thr Glu Glu Ala Lys Thr Phe Phe Ala Gly Met Ala Glu Lys
            115                 120                 125

Tyr Gly Glu Tyr Pro Asn Val Ile Tyr Glu Ile Trp Asn Glu Pro Asp
130                 135                 140

Tyr Phe Glu Trp Glu Glu Val Lys Thr Tyr Ser Glu Glu Val Ile Ala
145                 150                 155                 160

Val Ile Arg Ala Ile Asp Pro Asp Asn Ile Ile Leu Val Gly Ser Pro
                165                 170                 175

His Trp Asp Gln Asp Leu His Leu Val Ala Glu Asp Pro Ile Arg Asp
            180                 185                 190

Val Ser Asn Ile Met Tyr Thr Met His Phe Tyr Ala Ala Thr His Glu
            195                 200                 205

Ala Trp Leu Arg Asp Arg Thr Asp Glu Ala Ile Ala Lys Gly Ile Pro
            210                 215                 220

Val Phe Val Ser Glu Cys Gly Gly Ser Glu Ala Asn Gly Asp Gly Arg
225                 230                 235                 240

Leu Gly Ile Glu Glu Trp Lys Thr Tyr Val Asp Trp Met Glu Ser Arg
                245                 250                 255

Lys Ile Ser Trp Val Ala Trp Ser Val Ser Asp Lys Asn Glu Thr Cys
            260                 265                 270

Ser Met Leu Leu Pro Arg Ala Ser Ala Asp Gly Asn Trp Thr Glu Asp
            275                 280                 285

Leu Leu Lys Pro Trp Gly Lys Leu Thr Arg Asn Ser Ile Arg Asn Ala
            290                 295                 300
```

Asn Asp Glu Asn Pro Asp Ile
305             310

<210> SEQ ID NO 6
<211> LENGTH: 311
<212> TYPE: PRT
<213> ORGANISM: Artificial sequence
<220> FEATURE:
<223> OTHER INFORMATION: Sequence representing single alanine
      substitution made on SEQ ID NO 4 wherein cysteine 89 is replaced
      by alanine

<400> SEQUENCE: 6

Glu Asn Asn Arg Lys Thr Asp Tyr Arg Ser Ile Val Ala Gln Asn Gly
1               5                   10                  15

Arg Leu Gln Val Ile Gly Thr Gln Leu Ser Asn Glu Lys Gly Glu Pro
            20                  25                  30

Val Val Leu Arg Gly Ala Ser Leu Gly Trp His Asn Leu Trp Pro Arg
        35                  40                  45

Phe Tyr Asn Lys Asn Ala Val Gln Trp Leu Ala Asp Trp Lys Cys
    50                  55                  60

Thr Val Val Arg Ala Ala Met Gly Leu Glu Ile Glu Asp Asn Tyr Arg
65                  70                  75                  80

Glu Asn Pro Glu Phe Ala Leu Gln Ala Ile Thr Pro Val Ile Glu Ser
                85                  90                  95

Ala Ile Glu Asn Gly Ile Tyr Val Ile Ile Asp Phe His Ala His Asn
            100                 105                 110

Lys Tyr Thr Glu Glu Ala Lys Thr Phe Phe Ala Gly Met Ala Glu Lys
        115                 120                 125

Tyr Gly Glu Tyr Pro Asn Val Ile Tyr Glu Ile Trp Asn Glu Pro Asp
    130                 135                 140

Tyr Phe Glu Trp Glu Glu Val Lys Thr Tyr Ser Glu Glu Val Ile Ala
145                 150                 155                 160

Val Ile Arg Ala Ile Asp Pro Asp Asn Ile Ile Leu Val Gly Ser Pro
                165                 170                 175

His Trp Asp Gln Asp Leu His Leu Val Ala Glu Asp Pro Ile Arg Asp
            180                 185                 190

Val Ser Asn Ile Met Tyr Thr Met His Phe Tyr Ala Ala Thr His Glu
        195                 200                 205

Ala Trp Leu Arg Asp Arg Thr Asp Glu Ala Ile Ala Lys Gly Ile Pro
    210                 215                 220

Val Phe Val Ser Glu Cys Gly Gly Ser Glu Ala Asn Gly Asp Gly Arg
225                 230                 235                 240

Leu Gly Ile Glu Glu Trp Lys Thr Tyr Val Asp Trp Met Glu Ser Arg
                245                 250                 255

Lys Ile Ser Trp Val Ala Trp Ser Val Ser Asp Lys Asn Glu Thr Cys
            260                 265                 270

Ser Met Leu Leu Pro Arg Ala Ser Ala Asp Gly Asn Trp Thr Glu Asp
        275                 280                 285

Leu Leu Lys Pro Trp Gly Lys Leu Thr Arg Asn Ser Ile Arg Asn Ala
    290                 295                 300

Asn Asp Glu Asn Pro Asp Ile
305             310

<210> SEQ ID NO 7
<211> LENGTH: 311

<212> TYPE: PRT
<213> ORGANISM: Artificial sequence
<220> FEATURE:
<223> OTHER INFORMATION: Sequence representing single alanine
      substitution made on SEQ ID NO 4 wherein cysteine 230 is replaced
      by alanine

<400> SEQUENCE: 7

```
Glu Asn Asn Arg Lys Thr Asp Tyr Arg Ser Ile Val Ala Gln Asn Gly
 1               5                  10                  15

Arg Leu Gln Val Ile Gly Thr Gln Leu Ser Asn Glu Lys Gly Glu Pro
                20                  25                  30

Val Val Leu Arg Gly Ala Ser Leu Gly Trp His Asn Leu Trp Pro Arg
            35                  40                  45

Phe Tyr Asn Lys Asn Ala Val Gln Trp Leu Ala Asp Trp Lys Cys
 50                  55                  60

Thr Val Val Arg Ala Ala Met Gly Leu Glu Ile Glu Asp Asn Tyr Arg
 65                  70                  75                  80

Glu Asn Pro Glu Phe Ala Leu Gln Cys Ile Thr Pro Val Ile Glu Ser
                85                  90                  95

Ala Ile Glu Asn Gly Ile Tyr Val Ile Ile Asp Phe His Ala His Asn
            100                 105                 110

Lys Tyr Thr Glu Glu Ala Lys Thr Phe Phe Ala Gly Met Ala Glu Lys
        115                 120                 125

Tyr Gly Glu Tyr Pro Asn Val Ile Tyr Glu Ile Trp Asn Glu Pro Asp
130                 135                 140

Tyr Phe Glu Trp Glu Glu Val Lys Thr Tyr Ser Glu Glu Val Ile Ala
145                 150                 155                 160

Val Ile Arg Ala Ile Asp Pro Asp Asn Ile Ile Leu Val Gly Ser Pro
                165                 170                 175

His Trp Asp Gln Asp Leu His Leu Val Ala Glu Asp Pro Ile Arg Asp
            180                 185                 190

Val Ser Asn Ile Met Tyr Thr Met His Phe Tyr Ala Ala Thr His Glu
        195                 200                 205

Ala Trp Leu Arg Asp Arg Thr Asp Glu Ala Ile Ala Lys Gly Ile Pro
210                 215                 220

Val Phe Val Ser Glu Ala Gly Ser Glu Ala Asn Gly Asp Gly Arg
225                 230                 235                 240

Leu Gly Ile Glu Glu Trp Lys Thr Tyr Val Asp Trp Met Glu Ser Arg
                245                 250                 255

Lys Ile Ser Trp Val Ala Trp Ser Val Ser Lys Asn Glu Thr Cys
            260                 265                 270

Ser Met Leu Leu Pro Arg Ala Ser Ala Asp Gly Asn Trp Thr Glu Asp
        275                 280                 285

Leu Leu Lys Pro Trp Gly Lys Leu Thr Arg Asn Ser Ile Arg Asn Ala
290                 295                 300

Asn Asp Glu Asn Pro Asp Ile
305                 310
```

<210> SEQ ID NO 8
<211> LENGTH: 311
<212> TYPE: PRT
<213> ORGANISM: Artificial sequence
<220> FEATURE:
<223> OTHER INFORMATION: Sequence representing single alanine
      substitution made on SEQ ID NO 4 wherein cysteine 272 is replaced
      by alanine

<400> SEQUENCE: 8

Glu Asn Asn Arg Lys Thr Asp Tyr Arg Ser Ile Val Ala Gln Asn Gly
1               5                   10                  15

Arg Leu Gln Val Ile Gly Thr Gln Leu Ser Asn Glu Lys Gly Glu Pro
            20                  25                  30

Val Val Leu Arg Gly Ala Ser Leu Gly Trp His Asn Leu Trp Pro Arg
        35                  40                  45

Phe Tyr Asn Lys Asn Ala Val Gln Trp Leu Ala Asp Asp Trp Lys Cys
    50                  55                  60

Thr Val Val Arg Ala Ala Met Gly Leu Glu Ile Glu Asp Asn Tyr Arg
65                  70                  75                  80

Glu Asn Pro Glu Phe Ala Leu Gln Cys Ile Thr Pro Val Ile Glu Ser
                85                  90                  95

Ala Ile Glu Asn Gly Ile Tyr Val Ile Ile Asp Phe His Ala His Asn
            100                 105                 110

Lys Tyr Thr Glu Glu Ala Lys Thr Phe Phe Ala Gly Met Ala Glu Lys
        115                 120                 125

Tyr Gly Glu Tyr Pro Asn Val Ile Tyr Glu Ile Trp Asn Glu Pro Asp
    130                 135                 140

Tyr Phe Glu Trp Glu Glu Val Lys Thr Tyr Ser Glu Glu Val Ile Ala
145                 150                 155                 160

Val Ile Arg Ala Ile Asp Pro Asp Asn Ile Ile Leu Val Gly Ser Pro
                165                 170                 175

His Trp Asp Gln Asp Leu His Leu Val Ala Glu Asp Pro Ile Arg Asp
            180                 185                 190

Val Ser Asn Ile Met Tyr Thr Met His Phe Tyr Ala Ala Thr His Glu
        195                 200                 205

Ala Trp Leu Arg Asp Arg Thr Asp Glu Ala Ile Ala Lys Gly Ile Pro
    210                 215                 220

Val Phe Val Ser Glu Cys Gly Gly Ser Glu Ala Asn Gly Asp Gly Arg
225                 230                 235                 240

Leu Gly Ile Glu Glu Trp Lys Thr Tyr Val Asp Trp Met Glu Ser Arg
                245                 250                 255

Lys Ile Ser Trp Val Ala Trp Ser Val Ser Asp Lys Asn Glu Thr Ala
            260                 265                 270

Ser Met Leu Leu Pro Arg Ala Ser Ala Asp Gly Asn Trp Thr Glu Asp
        275                 280                 285

Leu Leu Lys Pro Trp Gly Lys Leu Thr Arg Asn Ser Ile Arg Asn Ala
    290                 295                 300

Asn Asp Glu Asn Pro Asp Ile
305                 310

<210> SEQ ID NO 9
<211> LENGTH: 311
<212> TYPE: PRT
<213> ORGANISM: Artificial sequence
<220> FEATURE:
<223> OTHER INFORMATION: Sequence representing double alanine
      substitutions made on SEQ ID NO 4 wherein cysteine 64 and 89 are
      replaced by alanine

<400> SEQUENCE: 9

Glu Asn Asn Arg Lys Thr Asp Tyr Arg Ser Ile Val Ala Gln Asn Gly
1               5                   10                  15

Arg Leu Gln Val Ile Gly Thr Gln Leu Ser Asn Glu Lys Gly Glu Pro
            20                  25                  30

Val Val Leu Arg Gly Ala Ser Leu Gly Trp His Asn Leu Trp Pro Arg
            35                  40                  45

Phe Tyr Asn Lys Asn Ala Val Gln Trp Leu Ala Asp Asp Trp Lys Ala
    50                  55                  60

Thr Val Val Arg Ala Ala Met Gly Leu Glu Ile Glu Asp Asn Tyr Arg
65                  70                  75                  80

Glu Asn Pro Glu Phe Ala Leu Gln Ala Ile Thr Pro Val Ile Glu Ser
                85                  90                  95

Ala Ile Glu Asn Gly Ile Tyr Val Ile Asp Phe His Ala His Asn
                100                 105                 110

Lys Tyr Thr Glu Ala Lys Thr Phe Phe Ala Gly Met Ala Glu Lys
            115                 120                 125

Tyr Gly Glu Tyr Pro Asn Val Ile Tyr Glu Ile Trp Asn Glu Pro Asp
            130                 135                 140

Tyr Phe Glu Trp Glu Glu Val Lys Thr Tyr Ser Glu Glu Val Ile Ala
145                 150                 155                 160

Val Ile Arg Ala Ile Asp Pro Asp Asn Ile Ile Leu Val Gly Ser Pro
                165                 170                 175

His Trp Asp Gln Asp Leu His Leu Val Ala Glu Asp Pro Ile Arg Asp
            180                 185                 190

Val Ser Asn Ile Met Tyr Thr Met His Phe Tyr Ala Ala Thr His Glu
            195                 200                 205

Ala Trp Leu Arg Asp Arg Thr Asp Glu Ala Ile Ala Lys Gly Ile Pro
        210                 215                 220

Val Phe Val Ser Glu Cys Gly Gly Ser Glu Ala Asn Gly Asp Gly Arg
225                 230                 235                 240

Leu Gly Ile Glu Glu Trp Lys Thr Tyr Val Asp Trp Met Glu Ser Arg
                245                 250                 255

Lys Ile Ser Trp Val Ala Trp Ser Val Ser Asp Lys Asn Glu Thr Cys
            260                 265                 270

Ser Met Leu Leu Pro Arg Ala Ser Ala Asp Gly Asn Trp Thr Glu Asp
            275                 280                 285

Leu Leu Lys Pro Trp Gly Lys Leu Thr Arg Asn Ser Ile Arg Asn Ala
        290                 295                 300

Asn Asp Glu Asn Pro Asp Ile
305                 310

<210> SEQ ID NO 10
<211> LENGTH: 311
<212> TYPE: PRT
<213> ORGANISM: Artificial sequence
<220> FEATURE:
<223> OTHER INFORMATION: Sequence representing double alanine
      substitutions made on SEQ ID NO 4 wherein cysteine 64 and 230 are
      replaced by alanine

<400> SEQUENCE: 10

Glu Asn Asn Arg Lys Thr Asp Tyr Arg Ser Ile Val Ala Gln Asn Gly
1               5                   10                  15

Arg Leu Gln Val Ile Gly Thr Gln Leu Ser Asn Glu Lys Gly Glu Pro
            20                  25                  30

Val Val Leu Arg Gly Ala Ser Leu Gly Trp His Asn Leu Trp Pro Arg
            35                  40                  45

Phe Tyr Asn Lys Asn Ala Val Gln Trp Leu Ala Asp Asp Trp Lys Ala
    50                  55                  60

Thr Val Val Arg Ala Ala Met Gly Leu Glu Ile Glu Asp Asn Tyr Arg
65                  70                  75                  80

Glu Asn Pro Glu Phe Ala Leu Gln Cys Ile Thr Pro Val Ile Glu Ser
            85                  90                  95

Ala Ile Glu Asn Gly Ile Tyr Val Ile Ile Asp Phe His Ala His Asn
        100                 105                 110

Lys Tyr Thr Glu Glu Ala Lys Thr Phe Phe Ala Gly Met Ala Glu Lys
    115                 120                 125

Tyr Gly Glu Tyr Pro Asn Val Ile Tyr Glu Ile Trp Asn Glu Pro Asp
130                 135                 140

Tyr Phe Glu Trp Glu Glu Val Lys Thr Tyr Ser Glu Glu Val Ile Ala
145                 150                 155                 160

Val Ile Arg Ala Ile Asp Pro Asp Asn Ile Ile Leu Val Gly Ser Pro
                165                 170                 175

His Trp Asp Gln Asp Leu His Leu Val Ala Glu Asp Pro Ile Arg Asp
            180                 185                 190

Val Ser Asn Ile Met Tyr Thr Met His Phe Tyr Ala Ala Thr His Glu
        195                 200                 205

Ala Trp Leu Arg Asp Arg Thr Asp Glu Ala Ile Ala Lys Gly Ile Pro
    210                 215                 220

Val Phe Val Ser Glu Ala Gly Gly Ser Glu Ala Asn Gly Asp Gly Arg
225                 230                 235                 240

Leu Gly Ile Glu Glu Trp Lys Thr Tyr Val Asp Trp Met Glu Ser Arg
                245                 250                 255

Lys Ile Ser Trp Val Ala Trp Ser Val Ser Asp Lys Asn Glu Thr Cys
            260                 265                 270

Ser Met Leu Leu Pro Arg Ala Ser Ala Asp Gly Asn Trp Thr Glu Asp
        275                 280                 285

Leu Leu Lys Pro Trp Gly Lys Leu Thr Arg Asn Ser Ile Arg Asn Ala
    290                 295                 300

Asn Asp Glu Asn Pro Asp Ile
305                 310

<210> SEQ ID NO 11
<211> LENGTH: 311
<212> TYPE: PRT
<213> ORGANISM: Artificial sequence
<220> FEATURE:
<223> OTHER INFORMATION: Sequence representing double alanine
      substitutions made on SEQ ID NO 4 wherein cysteine 64 and 272 are
      replaced by alanine

<400> SEQUENCE: 11

Glu Asn Asn Arg Lys Thr Asp Tyr Arg Ser Ile Val Ala Gln Asn Gly
1               5                   10                  15

Arg Leu Gln Val Ile Gly Thr Gln Leu Ser Asn Glu Lys Gly Glu Pro
                20                  25                  30

Val Val Leu Arg Gly Ala Ser Leu Gly Trp His Asn Leu Trp Pro Arg
            35                  40                  45

Phe Tyr Asn Lys Asn Ala Val Gln Trp Leu Ala Asp Trp Lys Ala
    50                  55                  60

Thr Val Val Arg Ala Ala Met Gly Leu Glu Ile Glu Asp Asn Tyr Arg
65                  70                  75                  80

Glu Asn Pro Glu Phe Ala Leu Gln Cys Ile Thr Pro Val Ile Glu Ser
            85                  90                  95

Ala Ile Glu Asn Gly Ile Tyr Val Ile Ile Asp Phe His Ala His Asn

```
                    100                 105                 110
Lys Tyr Thr Glu Glu Ala Lys Thr Phe Phe Ala Gly Met Ala Glu Lys
            115                 120                 125

Tyr Gly Glu Tyr Pro Asn Val Ile Tyr Glu Ile Trp Asn Glu Pro Asp
            130                 135                 140

Tyr Phe Glu Trp Glu Val Lys Thr Tyr Ser Glu Val Ile Ala
145                 150                 155                 160

Val Ile Arg Ala Ile Asp Pro Asp Asn Ile Ile Leu Val Gly Ser Pro
                165                 170                 175

His Trp Asp Gln Asp Leu His Leu Val Ala Glu Asp Pro Ile Arg Asp
                180                 185                 190

Val Ser Asn Ile Met Tyr Thr Met His Phe Tyr Ala Ala Thr His Glu
                195                 200                 205

Ala Trp Leu Arg Asp Arg Thr Asp Glu Ala Ile Ala Lys Gly Ile Pro
            210                 215                 220

Val Phe Val Ser Glu Cys Gly Gly Ser Glu Ala Asn Gly Asp Gly Arg
225                 230                 235                 240

Leu Gly Ile Glu Glu Trp Lys Thr Tyr Val Asp Trp Met Glu Ser Arg
                245                 250                 255

Lys Ile Ser Trp Val Ala Trp Ser Val Ser Asp Lys Asn Glu Thr Ala
                260                 265                 270

Ser Met Leu Leu Pro Arg Ala Ser Ala Asp Gly Asn Trp Thr Glu Asp
            275                 280                 285

Leu Leu Lys Pro Trp Gly Lys Leu Thr Arg Asn Ser Ile Arg Asn Ala
            290                 295                 300

Asn Asp Glu Asn Pro Asp Ile
305                 310

<210> SEQ ID NO 12
<211> LENGTH: 311
<212> TYPE: PRT
<213> ORGANISM: Artificial sequence
<220> FEATURE:
<223> OTHER INFORMATION: Sequence representing double alanine
      substitutions made on SEQ ID NO 4 wherein cysteine 89 and 230 are
      replaced by alanine

<400> SEQUENCE: 12

Glu Asn Asn Arg Lys Thr Asp Tyr Arg Ser Ile Val Ala Gln Asn Gly
1               5                   10                  15

Arg Leu Gln Val Ile Gly Thr Gln Leu Ser Asn Glu Lys Gly Glu Pro
            20                  25                  30

Val Val Leu Arg Gly Ala Ser Leu Gly Trp His Asn Leu Trp Pro Arg
        35                  40                  45

Phe Tyr Asn Lys Asn Ala Val Gln Trp Leu Ala Asp Asp Trp Lys Cys
    50                  55                  60

Thr Val Arg Ala Ala Met Gly Leu Glu Ile Glu Asp Asn Tyr Arg
65                  70                  75                  80

Glu Asn Pro Glu Phe Ala Leu Gln Ala Ile Thr Pro Val Ile Glu Ser
                85                  90                  95

Ala Ile Glu Asn Gly Ile Tyr Val Ile Ile Asp Phe His Ala His Asn
                100                 105                 110

Lys Tyr Thr Glu Glu Ala Lys Thr Phe Phe Ala Gly Met Ala Glu Lys
            115                 120                 125

Tyr Gly Glu Tyr Pro Asn Val Ile Tyr Glu Ile Trp Asn Glu Pro Asp
            130                 135                 140
```

```
Tyr Phe Glu Trp Glu Glu Val Lys Thr Tyr Ser Glu Glu Val Ile Ala
145                 150                 155                 160

Val Ile Arg Ala Ile Asp Pro Asp Asn Ile Ile Leu Val Gly Ser Pro
                165                 170                 175

His Trp Asp Gln Asp Leu His Leu Val Ala Glu Asp Pro Ile Arg Asp
            180                 185                 190

Val Ser Asn Ile Met Tyr Thr Met His Phe Tyr Ala Ala Thr His Glu
        195                 200                 205

Ala Trp Leu Arg Asp Arg Thr Asp Glu Ala Ile Ala Lys Gly Ile Pro
    210                 215                 220

Val Phe Val Ser Glu Ala Gly Gly Ser Glu Ala Asn Gly Asp Gly Arg
225                 230                 235                 240

Leu Gly Ile Glu Glu Trp Lys Thr Tyr Val Asp Trp Met Glu Ser Arg
                245                 250                 255

Lys Ile Ser Trp Val Ala Trp Ser Val Ser Asp Lys Asn Glu Thr Cys
                260                 265                 270

Ser Met Leu Leu Pro Arg Ala Ser Ala Asp Gly Asn Trp Thr Glu Asp
            275                 280                 285

Leu Leu Lys Pro Trp Gly Lys Leu Thr Arg Asn Ser Ile Arg Asn Ala
        290                 295                 300

Asn Asp Glu Asn Pro Asp Ile
305                 310

<210> SEQ ID NO 13
<211> LENGTH: 311
<212> TYPE: PRT
<213> ORGANISM: Artificial sequence
<220> FEATURE:
<223> OTHER INFORMATION: Sequence representing double alanine
      substitutions made on SEQ ID NO 4 wherein cysteine 89 and 272 are
      replaced by alanine

<400> SEQUENCE: 13

Glu Asn Asn Arg Lys Thr Asp Tyr Arg Ser Ile Val Ala Gln Asn Gly
1               5                   10                  15

Arg Leu Gln Val Ile Gly Thr Gln Leu Ser Asn Glu Lys Gly Glu Pro
                20                  25                  30

Val Val Leu Arg Gly Ala Ser Leu Gly Trp His Asn Leu Trp Pro Arg
            35                  40                  45

Phe Tyr Asn Lys Asn Ala Val Gln Trp Leu Ala Asp Asp Trp Lys Cys
    50                  55                  60

Thr Val Val Arg Ala Ala Met Gly Leu Glu Ile Glu Asp Asn Tyr Arg
65                  70                  75                  80

Glu Asn Pro Glu Phe Ala Leu Gln Ala Ile Thr Pro Val Ile Glu Ser
                85                  90                  95

Ala Ile Glu Asn Gly Ile Tyr Val Ile Asp Phe His Ala His Asn
            100                 105                 110

Lys Tyr Thr Glu Glu Ala Lys Thr Phe Phe Ala Gly Met Ala Glu Lys
        115                 120                 125

Tyr Gly Glu Tyr Pro Asn Val Ile Tyr Glu Ile Trp Asn Glu Pro Asp
    130                 135                 140

Tyr Phe Glu Trp Glu Glu Val Lys Thr Tyr Ser Glu Glu Val Ile Ala
145                 150                 155                 160

Val Ile Arg Ala Ile Asp Pro Asp Asn Ile Ile Leu Val Gly Ser Pro
                165                 170                 175
```

```
His Trp Asp Gln Asp Leu His Leu Val Ala Glu Asp Pro Ile Arg Asp
            180                 185                 190

Val Ser Asn Ile Met Tyr Thr Met His Phe Tyr Ala Ala Thr His Glu
        195                 200                 205

Ala Trp Leu Arg Asp Arg Thr Asp Glu Ala Ile Ala Lys Gly Ile Pro
    210                 215                 220

Val Phe Val Ser Glu Cys Gly Gly Ser Glu Ala Asn Gly Asp Gly Arg
225                 230                 235                 240

Leu Gly Ile Glu Glu Trp Lys Thr Tyr Val Asp Trp Met Glu Ser Arg
                245                 250                 255

Lys Ile Ser Trp Val Ala Trp Ser Val Ser Asp Lys Asn Glu Thr Ala
            260                 265                 270

Ser Met Leu Leu Pro Arg Ala Ser Ala Asp Gly Asn Trp Thr Glu Asp
        275                 280                 285

Leu Leu Lys Pro Trp Gly Lys Leu Thr Arg Asn Ser Ile Arg Asn Ala
    290                 295                 300

Asn Asp Glu Asn Pro Asp Ile
305                 310
```

<210> SEQ ID NO 14
<211> LENGTH: 311
<212> TYPE: PRT
<213> ORGANISM: Artificial sequence
<220> FEATURE:
<223> OTHER INFORMATION: Sequence representing double alanine
      substitutions made on SEQ ID NO 4 wherein cysteine 230 and 272
      are replaced by alanine

<400> SEQUENCE: 14

```
Glu Asn Asn Arg Lys Thr Asp Tyr Arg Ser Ile Val Ala Gln Asn Gly
1               5                   10                  15

Arg Leu Gln Val Ile Gly Thr Gln Leu Ser Asn Glu Lys Gly Glu Pro
            20                  25                  30

Val Val Leu Arg Gly Ala Ser Leu Gly Trp His Asn Leu Trp Pro Arg
        35                  40                  45

Phe Tyr Asn Lys Asn Ala Val Gln Trp Leu Ala Asp Asp Trp Lys Cys
    50                  55                  60

Thr Val Val Arg Ala Ala Met Gly Leu Glu Ile Glu Asp Asn Tyr Arg
65                  70                  75                  80

Glu Asn Pro Glu Phe Ala Leu Gln Cys Ile Thr Pro Val Ile Glu Ser
                85                  90                  95

Ala Ile Glu Asn Gly Ile Tyr Val Ile Asp Phe His Ala His Asn
            100                 105                 110

Lys Tyr Thr Glu Glu Ala Lys Thr Phe Phe Ala Gly Met Ala Glu Lys
        115                 120                 125

Tyr Gly Glu Tyr Pro Asn Val Ile Tyr Glu Ile Trp Asn Glu Pro Asp
    130                 135                 140

Tyr Phe Glu Trp Glu Glu Val Lys Thr Tyr Ser Glu Glu Val Ile Ala
145                 150                 155                 160

Val Ile Arg Ala Ile Asp Pro Asp Asn Ile Ile Leu Val Gly Ser Pro
                165                 170                 175

His Trp Asp Gln Asp Leu His Leu Val Ala Glu Asp Pro Ile Arg Asp
            180                 185                 190

Val Ser Asn Ile Met Tyr Thr Met His Phe Tyr Ala Ala Thr His Glu
        195                 200                 205

Ala Trp Leu Arg Asp Arg Thr Asp Glu Ala Ile Ala Lys Gly Ile Pro
```

```
            210                 215                 220
Val Phe Val Ser Glu Ala Gly Gly Ser Glu Ala Asn Gly Asp Gly Arg
225                 230                 235                 240

Leu Gly Ile Glu Glu Trp Lys Thr Tyr Val Asp Trp Met Glu Ser Arg
                245                 250                 255

Lys Ile Ser Trp Val Ala Trp Ser Val Ser Asp Lys Asn Glu Thr Ala
                260                 265                 270

Ser Met Leu Leu Pro Arg Ala Ser Ala Asp Gly Asn Trp Thr Glu Asp
                275                 280                 285

Leu Leu Lys Pro Trp Gly Lys Leu Thr Arg Asn Ser Ile Arg Asn Ala
                290                 295                 300

Asn Asp Glu Asn Pro Asp Ile
305                 310

<210> SEQ ID NO 15
<211> LENGTH: 311
<212> TYPE: PRT
<213> ORGANISM: Artificial sequence
<220> FEATURE:
<223> OTHER INFORMATION: Sequence representing triple alanine
      substitutions made on SEQ ID NO 4 wherein cysteine 64, 84 and 230
      are replaced by alanine

<400> SEQUENCE: 15

Glu Asn Asn Arg Lys Thr Asp Tyr Arg Ser Ile Val Ala Gln Asn Gly
1               5                   10                  15

Arg Leu Gln Val Ile Gly Thr Gln Leu Ser Asn Glu Lys Gly Glu Pro
                20                  25                  30

Val Val Leu Arg Gly Ala Ser Leu Gly Trp His Asn Leu Trp Pro Arg
                35                  40                  45

Phe Tyr Asn Lys Asn Ala Val Gln Trp Leu Ala Asp Asp Trp Lys Ala
50                  55                  60

Thr Val Val Arg Ala Ala Met Gly Leu Glu Ile Glu Asp Asn Tyr Arg
65                  70                  75                  80

Glu Asn Pro Glu Phe Ala Leu Gln Ala Ile Thr Pro Val Ile Glu Ser
                85                  90                  95

Ala Ile Glu Asn Gly Ile Tyr Val Ile Ile Asp Phe His Ala His Asn
                100                 105                 110

Lys Tyr Thr Glu Glu Ala Lys Thr Phe Phe Ala Gly Met Ala Glu Lys
                115                 120                 125

Tyr Gly Glu Tyr Pro Asn Val Ile Tyr Glu Ile Trp Asn Glu Pro Asp
                130                 135                 140

Tyr Phe Glu Trp Glu Glu Val Lys Thr Tyr Ser Glu Glu Val Ile Ala
145                 150                 155                 160

Val Ile Arg Ala Ile Asp Pro Asp Asn Ile Ile Leu Val Gly Ser Pro
                165                 170                 175

His Trp Asp Gln Asp Leu His Leu Val Ala Glu Asp Pro Ile Arg Asp
                180                 185                 190

Val Ser Asn Ile Met Tyr Thr Met His Phe Tyr Ala Ala Thr His Glu
                195                 200                 205

Ala Trp Leu Arg Asp Arg Thr Asp Glu Ala Ile Ala Lys Gly Ile Pro
                210                 215                 220

Val Phe Val Ser Glu Ala Gly Gly Ser Glu Ala Asn Gly Asp Gly Arg
225                 230                 235                 240

Leu Gly Ile Glu Glu Trp Lys Thr Tyr Val Asp Trp Met Glu Ser Arg
                245                 250                 255
```

```
Lys Ile Ser Trp Val Ala Trp Ser Val Ser Asp Lys Asn Glu Thr Cys
            260                 265                 270

Ser Met Leu Leu Pro Arg Ala Ser Ala Asp Gly Asn Trp Thr Glu Asp
        275                 280                 285

Leu Leu Lys Pro Trp Gly Lys Leu Thr Arg Asn Ser Ile Arg Asn Ala
290                 295                 300

Asn Asp Glu Asn Pro Asp Ile
305                 310

<210> SEQ ID NO 16
<211> LENGTH: 311
<212> TYPE: PRT
<213> ORGANISM: Artificial sequence
<220> FEATURE:
<223> OTHER INFORMATION: Sequence representing triple alanine
      substitutions made on SEQ ID NO 4 wherein cysteine 64,230 and 272
      are replaced by alanine

<400> SEQUENCE: 16

Glu Asn Asn Arg Lys Thr Asp Tyr Arg Ser Ile Val Ala Gln Asn Gly
1               5                   10                  15

Arg Leu Gln Val Ile Gly Thr Gln Leu Ser Asn Glu Lys Gly Glu Pro
            20                  25                  30

Val Val Leu Arg Gly Ala Ser Leu Gly Trp His Asn Leu Trp Pro Arg
        35                  40                  45

Phe Tyr Asn Lys Asn Ala Val Gln Trp Leu Ala Asp Asp Trp Lys Ala
    50                  55                  60

Thr Val Val Arg Ala Ala Met Gly Leu Glu Ile Glu Asp Asn Tyr Arg
65                  70                  75                  80

Glu Asn Pro Glu Phe Ala Leu Gln Cys Ile Thr Pro Val Ile Glu Ser
                85                  90                  95

Ala Ile Glu Asn Gly Ile Tyr Val Ile Asp Phe His Ala His Asn
            100                 105                 110

Lys Tyr Thr Glu Glu Ala Lys Thr Phe Phe Ala Gly Met Ala Glu Lys
        115                 120                 125

Tyr Gly Glu Tyr Pro Asn Val Ile Tyr Glu Ile Trp Asn Glu Pro Asp
    130                 135                 140

Tyr Phe Glu Trp Glu Glu Val Lys Thr Tyr Ser Glu Glu Val Ile Ala
145                 150                 155                 160

Val Ile Arg Ala Ile Asp Pro Asp Asn Ile Ile Leu Val Gly Ser Pro
                165                 170                 175

His Trp Asp Gln Asp Leu His Leu Val Ala Glu Asp Pro Ile Arg Asp
            180                 185                 190

Val Ser Asn Ile Met Tyr Thr Met His Phe Tyr Ala Ala Thr His Glu
        195                 200                 205

Ala Trp Leu Arg Asp Arg Thr Asp Glu Ala Ile Ala Lys Gly Ile Pro
    210                 215                 220

Val Phe Val Ser Glu Ala Gly Gly Ser Glu Ala Asn Gly Asp Gly Arg
225                 230                 235                 240

Leu Gly Ile Glu Glu Trp Lys Thr Tyr Val Asp Trp Met Glu Ser Arg
                245                 250                 255

Lys Ile Ser Trp Val Ala Trp Ser Val Ser Asp Lys Asn Glu Thr Ala
            260                 265                 270

Ser Met Leu Leu Pro Arg Ala Ser Ala Asp Gly Asn Trp Thr Glu Asp
        275                 280                 285
```

```
Leu Leu Lys Pro Trp Gly Lys Leu Thr Arg Asn Ser Ile Arg Asn Ala
        290                 295                 300

Asn Asp Glu Asn Pro Asp Ile
305                 310
```

<210> SEQ ID NO 17
<211> LENGTH: 311
<212> TYPE: PRT
<213> ORGANISM: Artificial sequence
<220> FEATURE:
<223> OTHER INFORMATION: Sequence representing triple alanine
      substitutions made on SEQ ID NO 4 wherein cysteine 89, 230 and 272
      are replaced by alanine

<400> SEQUENCE: 17

```
Glu Asn Asn Arg Lys Thr Asp Tyr Arg Ser Ile Val Ala Gln Asn Gly
1               5                   10                  15

Arg Leu Gln Val Ile Gly Thr Gln Leu Ser Asn Glu Lys Gly Glu Pro
            20                  25                  30

Val Val Leu Arg Gly Ala Ser Leu Gly Trp His Asn Leu Trp Pro Arg
        35                  40                  45

Phe Tyr Asn Lys Asn Ala Val Gln Trp Leu Ala Asp Asp Trp Lys Cys
    50                  55                  60

Thr Val Val Arg Ala Ala Met Gly Leu Glu Ile Glu Asp Asn Tyr Arg
65                  70                  75                  80

Glu Asn Pro Glu Phe Ala Leu Gln Ala Ile Thr Pro Val Ile Glu Ser
                85                  90                  95

Ala Ile Glu Asn Gly Ile Tyr Val Ile Ile Asp Phe His Ala His Asn
            100                 105                 110

Lys Tyr Thr Glu Glu Ala Lys Thr Phe Phe Ala Gly Met Ala Glu Lys
        115                 120                 125

Tyr Gly Glu Tyr Pro Asn Val Ile Tyr Glu Ile Trp Asn Glu Pro Asp
    130                 135                 140

Tyr Phe Glu Trp Glu Glu Val Lys Thr Tyr Ser Glu Glu Val Ile Ala
145                 150                 155                 160

Val Ile Arg Ala Ile Asp Pro Asp Asn Ile Ile Leu Val Gly Ser Pro
                165                 170                 175

His Trp Asp Gln Asp Leu His Leu Val Ala Glu Asp Pro Ile Arg Asp
            180                 185                 190

Val Ser Asn Ile Met Tyr Thr Met His Phe Tyr Ala Ala Thr His Glu
        195                 200                 205

Ala Trp Leu Arg Asp Arg Thr Asp Glu Ala Ile Ala Lys Gly Ile Pro
    210                 215                 220

Val Phe Val Ser Glu Ala Gly Gly Ser Glu Ala Asn Gly Asp Gly Arg
225                 230                 235                 240

Leu Gly Ile Glu Glu Trp Lys Thr Tyr Val Asp Trp Met Glu Ser Arg
                245                 250                 255

Lys Ile Ser Trp Val Ala Trp Ser Val Ser Asp Lys Asn Glu Thr Ala
            260                 265                 270

Ser Met Leu Leu Pro Arg Ala Ser Ala Asp Gly Asn Trp Thr Glu Asp
        275                 280                 285

Leu Leu Lys Pro Trp Gly Lys Leu Thr Arg Asn Ser Ile Arg Asn Ala
    290                 295                 300

Asn Asp Glu Asn Pro Asp Ile
305                 310
```

<210> SEQ ID NO 18
<211> LENGTH: 311
<212> TYPE: PRT
<213> ORGANISM: Artificial sequence
<220> FEATURE:
<223> OTHER INFORMATION: Sequence representing triple alanine substitutions made on SEQ ID NO 4 wherein cysteine 64,89 and 272 are replaced by alanine

<400> SEQUENCE: 18

```
Glu Asn Asn Arg Lys Thr Asp Tyr Arg Ser Ile Val Ala Gln Asn Gly
1               5                   10                  15

Arg Leu Gln Val Ile Gly Thr Gln Leu Ser Asn Glu Lys Gly Glu Pro
            20                  25                  30

Val Val Leu Arg Gly Ala Ser Leu Gly Trp His Asn Leu Trp Pro Arg
        35                  40                  45

Phe Tyr Asn Lys Asn Ala Val Gln Trp Leu Ala Asp Asp Trp Lys Ala
    50                  55                  60

Thr Val Val Arg Ala Ala Met Gly Leu Glu Ile Glu Asp Asn Tyr Arg
65                  70                  75                  80

Glu Asn Pro Glu Phe Ala Leu Gln Ala Ile Thr Pro Val Ile Glu Ser
                85                  90                  95

Ala Ile Glu Asn Gly Ile Tyr Val Ile Ile Asp Phe His Ala His Asn
            100                 105                 110

Lys Tyr Thr Glu Glu Ala Lys Thr Phe Phe Ala Gly Met Ala Glu Lys
        115                 120                 125

Tyr Gly Glu Tyr Pro Asn Val Ile Tyr Glu Ile Trp Asn Glu Pro Asp
    130                 135                 140

Tyr Phe Glu Trp Glu Glu Val Lys Thr Tyr Ser Glu Glu Val Ile Ala
145                 150                 155                 160

Val Ile Arg Ala Ile Asp Pro Asp Asn Ile Ile Leu Val Gly Ser Pro
                165                 170                 175

His Trp Asp Gln Asp Leu His Leu Val Ala Glu Asp Pro Ile Arg Asp
            180                 185                 190

Val Ser Asn Ile Met Tyr Thr Met His Phe Tyr Ala Ala Thr His Glu
        195                 200                 205

Ala Trp Leu Arg Asp Arg Thr Asp Glu Ala Ile Ala Lys Gly Ile Pro
    210                 215                 220

Val Phe Val Ser Glu Cys Gly Ser Glu Ala Asn Gly Asp Gly Arg
225                 230                 235                 240

Leu Gly Ile Glu Glu Trp Lys Thr Tyr Val Asp Trp Met Glu Ser Arg
                245                 250                 255

Lys Ile Ser Trp Val Ala Trp Ser Val Ser Asp Lys Asn Glu Thr Ala
            260                 265                 270

Ser Met Leu Leu Pro Arg Ala Ser Ala Asp Gly Asn Trp Thr Glu Asp
        275                 280                 285

Leu Leu Lys Pro Trp Gly Lys Leu Thr Arg Asn Ser Ile Arg Asn Ala
    290                 295                 300

Asn Asp Glu Asn Pro Asp Ile
305                 310
```

<210> SEQ ID NO 19
<211> LENGTH: 311
<212> TYPE: PRT
<213> ORGANISM: Artificial sequence
<220> FEATURE:
<223> OTHER INFORMATION: Sequence representing quadruple alanine substitutions made on SEQ ID NO 4 wherein cysteine 64, 89, 230 and 272 are replaced by alanine

<400> SEQUENCE: 19

```
Glu Asn Asn Arg Lys Thr Asp Tyr Arg Ser Ile Val Ala Gln Asn Gly
1               5                   10                  15

Arg Leu Gln Val Ile Gly Thr Gln Leu Ser Asn Glu Lys Gly Glu Pro
            20                  25                  30

Val Val Leu Arg Gly Ala Ser Leu Gly Trp His Asn Leu Trp Pro Arg
        35                  40                  45

Phe Tyr Asn Lys Asn Ala Val Gln Trp Leu Ala Asp Asp Trp Lys Ala
50                  55                  60

Thr Val Val Arg Ala Ala Met Gly Leu Glu Ile Glu Asp Asn Tyr Arg
65                  70                  75                  80

Glu Asn Pro Glu Phe Ala Leu Gln Ala Ile Thr Pro Val Ile Glu Ser
                85                  90                  95

Ala Ile Glu Asn Gly Ile Tyr Val Ile Asp Phe His Ala His Asn
            100                 105                 110

Lys Tyr Thr Glu Glu Ala Lys Thr Phe Phe Ala Gly Met Ala Glu Lys
        115                 120                 125

Tyr Gly Glu Tyr Pro Asn Val Ile Tyr Glu Ile Trp Asn Glu Pro Asp
130                 135                 140

Tyr Phe Glu Trp Glu Glu Val Lys Thr Tyr Ser Glu Glu Val Ile Ala
145                 150                 155                 160

Val Ile Arg Ala Ile Asp Pro Asp Asn Ile Ile Leu Val Gly Ser Pro
                165                 170                 175

His Trp Asp Gln Asp Leu His Leu Val Ala Glu Asp Pro Ile Arg Asp
            180                 185                 190

Val Ser Asn Ile Met Tyr Thr Met His Phe Tyr Ala Ala Thr His Glu
        195                 200                 205

Ala Trp Leu Arg Asp Arg Thr Asp Glu Ala Ile Ala Lys Gly Ile Pro
210                 215                 220

Val Phe Val Ser Glu Ala Gly Gly Ser Glu Ala Asn Gly Asp Gly Arg
225                 230                 235                 240

Leu Gly Ile Glu Glu Trp Lys Thr Tyr Val Asp Trp Met Glu Ser Arg
                245                 250                 255

Lys Ile Ser Trp Val Ala Trp Ser Val Ser Asp Lys Asn Glu Thr Ala
            260                 265                 270

Ser Met Leu Leu Pro Arg Ala Ser Ala Asp Gly Asn Trp Thr Glu Asp
        275                 280                 285

Leu Leu Lys Pro Trp Gly Lys Leu Thr Arg Asn Ser Ile Arg Asn Ala
290                 295                 300

Asn Asp Glu Asn Pro Asp Ile
305                 310
```

<210> SEQ ID NO 20
<211> LENGTH: 33
<212> TYPE: DNA
<213> ORGANISM: Artificial sequence
<220> FEATURE:
<223> OTHER INFORMATION: forward primer for amplification of full length gene
<220> FEATURE:
<221> NAME/KEY: primer
<222> LOCATION: (1)..(33)
<223> OTHER INFORMATION: synthetically generated primer for amplification of full length gene
<300> PUBLICATION INFORMATION:
<313> RELEVANT RESIDUES IN SEQ ID NO: (1)..(33)

```
<400> SEQUENCE: 20
aatatacata tgaagaaaaa ctcaatcatt ctc                                33

<210> SEQ ID NO 21
<211> LENGTH: 33
<212> TYPE: DNA
<213> ORGANISM: Artificial sequence
<220> FEATURE:
<223> OTHER INFORMATION: synthetically generated primer
<220> FEATURE:
<221> NAME/KEY: primer
<222> LOCATION: (1)..(33)
<223> OTHER INFORMATION: synthetically generated primer for
      amplification of full length gene
<300> PUBLICATION INFORMATION:
<313> RELEVANT RESIDUES IN SEQ ID NO: (1)..(33)

<400> SEQUENCE: 21
aatataggat cctcagatat ccgggttttc atc                                33

<210> SEQ ID NO 22
<211> LENGTH: 35
<212> TYPE: DNA
<213> ORGANISM: artificial sequence
<220> FEATURE:
<223> OTHER INFORMATION: synthetically generated primer
<220> FEATURE:
<221> NAME/KEY: primer
<222> LOCATION: (1)..(35)
<223> OTHER INFORMATION: synthetically generated forward primer for
      amplification of truncated gene

<400> SEQUENCE: 22
aatatacata tggaaaacaa caggaaaacg gacta                              35

<210> SEQ ID NO 23
<211> LENGTH: 24
<212> TYPE: DNA
<213> ORGANISM: artificial sequence
<220> FEATURE:
<223> OTHER INFORMATION: synthetically generated primer
<220> FEATURE:
<221> NAME/KEY: primer
<222> LOCATION: (1)..(24)
<223> OTHER INFORMATION: synthetically generated forward primer for
      Cys64Ala

<400> SEQUENCE: 23
cgattggaaa gcgacggtcg tcag                                          24

<210> SEQ ID NO 24
<211> LENGTH: 24
<212> TYPE: DNA
<213> ORGANISM: Artificial sequence
<220> FEATURE:
<223> OTHER INFORMATION: synthetically generated primer
<220> FEATURE:
<221> NAME/KEY: primer
<222> LOCATION: (1)..(24)
<223> OTHER INFORMATION: synthetically generated reverse primer for
      Cys64Ala

<400> SEQUENCE: 24
ctgacgaccg tcgctttcca atcg                                          24

<210> SEQ ID NO 25
<211> LENGTH: 28
<212> TYPE: DNA
```

```
<213> ORGANISM: artificial sequence
<220> FEATURE:
<223> OTHER INFORMATION: synthetically generated primer
<220> FEATURE:
<221> NAME/KEY: primer
<222> LOCATION: (1)..(28)
<223> OTHER INFORMATION: synthetically generated forward primer for
      Cys89Ala

<400> SEQUENCE: 25
gaatttgcct tacaggcgat cacccctg                                    28

<210> SEQ ID NO 26
<211> LENGTH: 28
<212> TYPE: DNA
<213> ORGANISM: artificial sequence
<220> FEATURE:
<223> OTHER INFORMATION: synthetically generated primer
<220> FEATURE:
<221> NAME/KEY: primer
<222> LOCATION: (1)..(28)
<223> OTHER INFORMATION: synthetically generated reverse primer for
      Cys89Ala

<400> SEQUENCE: 26
caggggtgat cgcctgtaag gcaaattc                                    28

<210> SEQ ID NO 27
<211> LENGTH: 21
<212> TYPE: DNA
<213> ORGANISM: Aartificial sequence
<220> FEATURE:
<221> NAME/KEY: primer
<222> LOCATION: (1)..(21)
<223> OTHER INFORMATION: syntheically generated forward primer sequence
      for Cys230Ala

<400> SEQUENCE: 27
cgtatcggag gcgggcggct c                                           21

<210> SEQ ID NO 28
<211> LENGTH: 21
<212> TYPE: DNA
<213> ORGANISM: Artificial sequence
<220> FEATURE:
<223> OTHER INFORMATION: synthetically generated primer
<220> FEATURE:
<221> NAME/KEY: primer
<222> LOCATION: (1)..(21)
<223> OTHER INFORMATION: syntheically generated forward primer sequence
      for Cys230Ala
<220> FEATURE:
<221> NAME/KEY: primer
<222> LOCATION: (1)..(21)
<223> OTHER INFORMATION: syntheically generated reverse primer sequence
      for Cys230Ala

<400> SEQUENCE: 28
gagccgcccg cctccgatac g                                           21

<210> SEQ ID NO 29
<211> LENGTH: 25
<212> TYPE: DNA
<213> ORGANISM: artificial sequence
<220> FEATURE:
<223> OTHER INFORMATION: synthetically generated primer
<220> FEATURE:
<221> NAME/KEY: primer1
<222> LOCATION: (1)..(25)
<223> OTHER INFORMATION: syntheically generated forward primer sequence
      for Cys272Ala
```

<400> SEQUENCE: 29
gaacgaaacc gcgtccatgc tgctc                                          25

<210> SEQ ID NO 30
<211> LENGTH: 25
<212> TYPE: DNA
<213> ORGANISM: artificial sequence
<220> FEATURE:
<223> OTHER INFORMATION: synthetically generated primer
<220> FEATURE:
<221> NAME/KEY: primer
<222> LOCATION: (1)..(25)
<223> OTHER INFORMATION: syntheically generated reverse primer sequence
      for Cys272Ala

<400> SEQUENCE: 30
gagcagcatg gacgcggttt cgttc                                          25

<210> SEQ ID NO 31
<211> LENGTH: 936
<212> TYPE: DNA
<213> ORGANISM: Artificial sequence
<220> FEATURE:
<223> OTHER INFORMATION: Nucleotide sequence representing single alanine
      substitution made on SEQ ID NO: 3 wherein the codon for cysteine
      at position 190 is replaced by alanine

<400> SEQUENCE: 31
gaaaacaaca ggaaaacgga ctaccgttcc atcgtagcgc agaacggccg tttacaggtg    60
atcggcacac aattgagcaa tgaaaaaggc gaacccgtcg ttttacgggg agccagcctc   120
ggatggcaca acctctggcc ccgcttctat aacaagaacg cggtgcaatg gctggccgac   180
gattggaaag cgacggtcgt cagggctgca atgggcttgg aaattgaaga caactaccgg   240
gaaaatcccg aatttgcctt acagtgcatc accctgtca tcgaatcggc tattgaaaac    300
ggaatctatg tgattatcga cttccacgca cacaacaaat acaccgaaga agccaaaaca   360
ttctttgccg ggatggccga aaaatacggg gaatatccga acgtgatcta tgaaatctgg   420
aacgaacccg attatttcga atgggaagaa gtaaaaaccct attcggaaga agtgatcgcc   480
gtcatccgcg cgatcgaccc cgacaatatt atattggtcg gcagccccca ttgggaccag   540
gacctgcatc tggtagccga agacccgatc cgggatgtaa gcaacatcat gtacaccatg   600 cattttacg ccgcgaccca cgaggcctgg ctgcgtgacc ggaccgacga ggcgattgcc    660
aaaggaattc ccgttttcgt atcggagtgc ggcggctcgg aagccaatgg cgacggacgg   720
ttaggcatag aagaatggaa aacctacgtc gattggatgg agagtcggaa aataagctgg   780
gtggcctggt ccgtttccga caagaacgaa acctgctcca tgctgctccc ccgcgcctct   840
gccgatggca actggacgga agacctgctc aagccttggg gaaaactgac gcgtaattct   900
atccggaacg cgaatgatga aaacccggat atctga                            936

<210> SEQ ID NO 32
<211> LENGTH: 936
<212> TYPE: DNA
<213> ORGANISM: Artificial sequence
<220> FEATURE:
<223> OTHER INFORMATION: Nucleotide sequence representing single alanine
      substitution made on SEQ ID NO: 3 wherein the codon for cysteine
      at position 265 is replaced by alanine

<400> SEQUENCE: 32
gaaaacaaca ggaaaacgga ctaccgttcc atcgtagcgc agaacggccg tttacaggtg    60

```
atcggcacac aattgagcaa tgaaaaaggc gaacccgtcg ttttacgggg agccagcctc    120
ggatggcaca acctctggcc ccgcttctat aacaagaacg cggtgcaatg gctggccgac    180
gattggaaat gcacggtcgt cagggctgca atgggcttgg aaattgaaga caactaccgg    240
gaaaatcccg aatttgcctt acaggcgatc acccctgtca tcgaatcggc tattgaaaac    300
ggaatctatg tgattatcga cttccacgca cacaacaaat acaccgaaga agccaaaaca    360
ttctttgccg ggatggccga aaaatacggg gaatatccga acgtgatcta tgaaatctgg    420
aacgaacccg attatttcga atgggaagaa gtaaaaacct attcggaaga agtgatcgcc    480
gtcatccgcg cgatcgaccc cgacaatatt atattggtcg gcagcccccca ttgggaccag    540 gacctgcatc tggtagccga agacccgatc cgggatgtaa gcaacatcat gtacaccatg    600 cattttacg ccgcgaccca cgaggcctgg ctgcgtgacc ggaccgacga ggcgattgcc    660
aaaggaattc ccgttttcgt atcggagtgc ggcggctcgg aagccaatgg cgacggacgg    720
ttaggcatag aagaatggaa aacctacgtc gattggatgg agagtcggaa aataagctgg    780
gtggcctggt ccgtttccga caagaacgaa acctgctcca tgctgctccc ccgcgcctct    840
gccgatggca actggacgga agacctgctc aagccttggg gaaaactgac gcgtaattct    900
atccggaacg cgaatgatga aaacccggat atctga                              936
```

<210> SEQ ID NO 33
<211> LENGTH: 936
<212> TYPE: DNA
<213> ORGANISM: Artificial sequence
<220> FEATURE:
<223> OTHER INFORMATION: Nucleotide sequence representing single alanine
      substitution made on SEQ ID NO: 3 wherein the codon for cysteine
      at position 688 is replaced by alanine

<400> SEQUENCE: 33

```
gaaaacaaca ggaaaacgga ctaccgttcc atcgtagcgc agaacggccg tttacaggtg     60
atcggcacac aattgagcaa tgaaaaaggc gaacccgtcg ttttacgggg agccagcctc    120
ggatggcaca acctctggcc ccgcttctat aacaagaacg cggtgcaatg gctggccgac    180
gattggaaat gcacggtcgt cagggctgca atgggcttgg aaattgaaga caactaccgg    240
gaaaatcccg aatttgcctt acagtgcatc accctgtca tcgaatcggc tattgaaaac    300
ggaatctatg tgattatcga cttccacgca cacaacaaat acaccgaaga agccaaaaca    360
ttctttgccg ggatggccga aaaatacggg gaatatccga acgtgatcta tgaaatctgg    420
aacgaacccg attatttcga atgggaagaa gtaaaaacct attcggaaga agtgatcgcc    480
gtcatccgcg cgatcgaccc cgacaatatt atattggtcg gcagcccccca ttgggaccag    540 gacctgcatc tggtagccga agacccgatc cgggatgtaa gcaacatcat gtacaccatg    600 cattttacg ccgcgaccca cgaggcctgg ctgcgtgacc ggaccgacga ggcgattgcc    660
aaaggaattc ccgttttcgt atcggaggcg ggcggctcgg aagccaatgg cgacggacgg    720
ttaggcatag aagaatggaa aacctacgtc gattggatgg agagtcggaa aataagctgg    780
gtggcctggt ccgtttccga caagaacgaa acctgctcca tgctgctccc ccgcgcctct    840
gccgatggca actggacgga agacctgctc aagccttggg gaaaactgac gcgtaattct    900
atccggaacg cgaatgatga aaacccggat atctga                              936
```

<210> SEQ ID NO 34
<211> LENGTH: 936
<212> TYPE: DNA

<213> ORGANISM: Artificial sequence
<220> FEATURE:
<223> OTHER INFORMATION: Nucleotide sequence representing single alanine substitution made on SEQ ID NO: 3 wherein the codon for cysteine at position 814 is replaced by alanine

<400> SEQUENCE: 34

```
gaaaacaaca ggaaaacgga ctaccgttcc atcgtagcgc agaacggccg tttacaggtg    60
atcggcacac aattgagcaa tgaaaaaggc gaacccgtcg ttttacgggg agccagcctc   120
ggatggcaca acctctggcc ccgcttctat aacaagaacg cggtgcaatg gctggccgac   180
gattggaaat gcacggtcgt cagggctgca atgggcttgg aaattgaaga caactaccgg   240
gaaaatcccg aatttgcctt acagtgcatc accccctgtca tcgaatcggc tattgaaaac   300
ggaatctatg tgattatcga cttccacgca cacaacaaat acaccgaaga agccaaaaca   360
ttctttgccg ggatggccga aaaatacggg gaatatccga acgtgatcta tgaaatctgg   420
aacgaacccg attatttcga atgggaagaa gtaaaaacct attcggaaga agtgatcgcc   480
gtcatccgcg cgatcgaccc cgacaatatt atattggtcg gcagccccca ttgggaccag   540
gacctgcatc tggtagccga agacccgatc cgggatgtaa gcaacatcat gtacaccatg   600
catttttacg ccgcgaccca cgaggcctgg ctgcgtgacc ggaccgacga ggcgattgcc   660
aaaggaattc ccgttttcgt atcggagtgc ggcggctcgg aagccaatgg cgacggacgg   720
ttaggcatag aagaatggaa aacctacgtc gattggatgg agagtcggaa aataagctgg   780
gtggcctggt ccgtttccga caagaacgaa accgcgtcca tgctgctccc ccgcgcctct   840
gccgatggca actggacgga agacctgctc aagccttggg gaaaactgac gcgtaattct   900
atccggaacg cgaatgatga aaacccggat atctga                             936
```

<210> SEQ ID NO 35
<211> LENGTH: 936
<212> TYPE: DNA
<213> ORGANISM: Artificial sequence
<220> FEATURE:
<223> OTHER INFORMATION: Nucleotide sequence representing double alanine substitutions made on SEQ ID NO: 3 wherein the codon for cysteine at positions 190 and 265 are replaced by alanine

<400> SEQUENCE: 35

```
gaaaacaaca ggaaaacgga ctaccgttcc atcgtagcgc agaacggccg tttacaggtg    60
atcggcacac aattgagcaa tgaaaaaggc gaacccgtcg ttttacgggg agccagcctc   120
ggatggcaca acctctggcc ccgcttctat aacaagaacg cggtgcaatg gctggccgac   180
gattggaaag cgacggtcgt cagggctgca atgggcttgg aaattgaaga caactaccgg   240
gaaaatcccg aatttgcctt acaggcgatc accccctgtca tcgaatcggc tattgaaaac   300
ggaatctatg tgattatcga cttccacgca cacaacaaat acaccgaaga agccaaaaca   360
ttctttgccg ggatggccga aaaatacggg gaatatccga acgtgatcta tgaaatctgg   420
aacgaacccg attatttcga atgggaagaa gtaaaaacct attcggaaga agtgatcgcc   480
gtcatccgcg cgatcgaccc cgacaatatt atattggtcg gcagccccca ttgggaccag   540
gacctgcatc tggtagccga agacccgatc cgggatgtaa gcaacatcat gtacaccatg   600
catttttacg ccgcgaccca cgaggcctgg ctgcgtgacc ggaccgacga ggcgattgcc   660
aaaggaattc ccgttttcgt atcggagtgc ggcggctcgg aagccaatgg cgacggacgg   720
ttaggcatag aagaatggaa aacctacgtc gattggatgg agagtcggaa aataagctgg   780
gtggcctggt ccgtttccga caagaacgaa accgctcca tgctgctccc ccgcgcctct    840
```

```
gccgatggca actggacgga agacctgctc aagccttggg aaaactgac gcgtaattct    900 atccggaacg cgaatgatga aaacccggat atctga                             936
```

<210> SEQ ID NO 36
<211> LENGTH: 936
<212> TYPE: DNA
<213> ORGANISM: Artificial sequence
<220> FEATURE:
<223> OTHER INFORMATION: Nucleotide sequence representing double alanine
      substitutions made on SEQ ID NO: 3 wherein the codon for cysteine
      at positions 190 and 688 are replaced by alanine

<400> SEQUENCE: 36

```
gaaaacaaca ggaaaacgga ctaccgttcc atcgtagcgc agaacggccg tttacaggtg    60
atcggcacac aattgagcaa tgaaaaaggc gaacccgtcg ttttacgggg agccagcctc   120
ggatggcaca acctctggcc ccgcttctat aacaagaacg cggtgcaatg ctggccgac    180 gattggaaag cgacggtcgt cagggctgca atgggcttgg aaattgaaga caactaccgg   240
gaaaatcccg aatttgcctt acagtgcatc accccctgtca tcgaatcggc tattgaaaac   300
ggaatctatg tgattatcga cttccacgca cacaacaaat acaccgaaga agccaaaaca   360
ttctttgccg ggatggccga aaaatacggg gaatatccga acgtgatcta tgaaatctgg   420
aacgaacccg attatttcga atgggaagaa gtaaaaaccct attcggaaga agtgatcgcc   480
gtcatccgcg cgatcgaccc cgacaatatt atattggtcg gcagccccca ttgggaccag   540
gacctgcatc tggtagccga agacccgatc cgggatgtaa gcaacatcat gtacaccatg   600 cattttacg ccgcgaccca cgaggcctgg ctgcgtgacc ggaccgacga ggcgattgcc   660
aaaggaattc ccgttttcgt atcggaggcg ggcggctcgg aagccaatgg cgacggacgg   720
ttaggcatag aagaatggaa aacctacgtc gattggatgg agagtcggaa ataagctgg    780 gtggcctggt ccgtttccga caagaacgaa acctgctcca tgctgctccc ccgcgcctct   840
gccgatggca actggacgga agacctgctc aagccttggg aaaactgac gcgtaattct    900 atccggaacg cgaatgatga aaacccggat atctga                             936
```

<210> SEQ ID NO 37
<211> LENGTH: 936
<212> TYPE: DNA
<213> ORGANISM: Artificial sequence
<220> FEATURE:
<223> OTHER INFORMATION: Nucleotide sequence representing double alanine
      substitutions made on SEQ ID NO: 3 wherein the codon for cysteine
      at positions 190 and 814 are replaced by alanine

<400> SEQUENCE: 37

```
gaaaacaaca ggaaaacgga ctaccgttcc atcgtagcgc agaacggccg tttacaggtg    60
atcggcacac aattgagcaa tgaaaaaggc gaacccgtcg ttttacgggg agccagcctc   120
ggatggcaca acctctggcc ccgcttctat aacaagaacg cggtgcaatg ctggccgac    180 gattggaaag cgacggtcgt cagggctgca atgggcttgg aaattgaaga caactaccgg   240
gaaaatcccg aatttgcctt acagtgcatc accccctgtca tcgaatcggc tattgaaaac   300
ggaatctatg tgattatcga cttccacgca cacaacaaat acaccgaaga agccaaaaca   360
ttctttgccg ggatggccga aaaatacggg gaatatccga acgtgatcta tgaaatctgg   420
aacgaacccg attatttcga atgggaagaa gtaaaaaccct attcggaaga agtgatcgcc   480
gtcatccgcg cgatcgaccc cgacaatatt atattggtcg gcagccccca ttgggaccag   540
```

```
gacctgcatc tggtagccga agacccgatc cgggatgtaa gcaacatcat gtacaccatg    600 cattttttacg ccgcgaccca cgaggcctgg ctgcgtgacc ggaccgacga ggcgattgcc   660
aaaggaattc ccgttttcgt atcggagtgc ggcggctcgg aagccaatgg cgacggacgg   720
ttaggcatag aagaatggaa aacctacgtc gattggatgg agagtcggaa aataagctgg   780
gtggcctggt ccgtttccga caagaacgaa accgcgtcca tgctgctccc ccgcgcctct   840
gccgatggca actggacgga agacctgctc aagccttggg gaaaactgac gcgtaattct   900
atccggaacg cgaatgatga aaacccggat atctga                             936
```

<210> SEQ ID NO 38
<211> LENGTH: 936
<212> TYPE: DNA
<213> ORGANISM: Artificial sequence
<220> FEATURE:
<223> OTHER INFORMATION: Nucleotide sequence representing double alanine
      substitutions made on SEQ ID NO: 3 wherein the codon for cysteine
      at positions 265 and 688 are replaced by alanine

<400> SEQUENCE: 38

```
gaaaacaaca ggaaaacgga ctaccgttcc atcgtagcgc agaacggccg tttacaggtg    60
atcggcacac aattgagcaa tgaaaaaggc gaacccgtcg ttttacgggg agccagcctc   120
ggatggcaca acctctggcc ccgcttctat aacaagaacg cggtgcaatg gctggccgac   180
gattggaaat gcacggtcgt cagggctgca atgggcttgg aaattgaaga caactaccgg   240
gaaaatcccg aatttgcctt acaggcgatc accccctgtca tcgaatcggc tattgaaaac   300
ggaatctatg tgattatcga cttccacgca cacaacaaat acaccgaaga agccaaaaca   360
ttctttgccg ggatggccga aaaatacggg gaatatccga acgtgatcta tgaaatctgg   420
aacgaacccg attatttcga atgggaagaa gtaaaaaccct attcggaaga agtgatcgcc   480
gtcatccgcg cgatcgaccc cgacaatatt atattggtcg gcagcccccca ttgggaccag   540 gacctgcatc tggtagccga agacccgatc cgggatgtaa gcaacatcat gtacaccatg   600 cattttttacg ccgcgaccca cgaggcctgg ctgcgtgacc ggaccgacga ggcgattgcc   660
aaaggaattc ccgttttcgt atcggagcgc ggcggctcgg aagccaatgg cgacggacgg   720
ttaggcatag aagaatggaa aacctacgtc gattggatgg agagtcggaa aataagctgg   780
gtggcctggt ccgtttccga caagaacgaa acctgctcca tgctgctccc ccgcgcctct   840
gccgatggca actggacgga agacctgctc aagccttggg gaaaactgac gcgtaattct   900
atccggaacg cgaatgatga aaacccggat atctga                             936
```

<210> SEQ ID NO 39
<211> LENGTH: 936
<212> TYPE: DNA
<213> ORGANISM: Artificial sequence
<220> FEATURE:
<223> OTHER INFORMATION: Nucleotide sequence representing double alanine
      substitutions made on SEQ ID NO: 3 wherein the codon for cysteine
      at positions 265 and 814 are replaced by alanine

<400> SEQUENCE: 39

```
gaaaacaaca ggaaaacgga ctaccgttcc atcgtagcgc agaacggccg tttacaggtg    60
atcggcacac aattgagcaa tgaaaaaggc gaacccgtcg ttttacgggg agccagcctc   120
ggatggcaca acctctggcc ccgcttctat aacaagaacg cggtgcaatg gctggccgac   180
gattggaaat gcacggtcgt cagggctgca atgggcttgg aaattgaaga caactaccgg   240
gaaaatcccg aatttgcctt acaggcgatc accccctgtca tcgaatcggc tattgaaaac   300
```

```
ggaatctatg tgattatcga cttccacgca cacaacaaat acaccgaaga agccaaaaca    360
ttctttgccg ggatggccga aaaatacggg gaatatccga acgtgatcta tgaaatctgg    420
aacgaacccg attatttcga atgggaagaa gtaaaaacct attcggaaga agtgatcgcc    480
gtcatccgcg cgatcgaccc cgacaatatt atattggtcg gcagccccca ttgggaccag    540
gacctgcatc tggtagccga agacccgatc cgggatgtaa gcaacatcat gtacaccatg    600 cattttacg ccgcgaccca cgaggcctgg ctgcgtgacc ggaccgacga ggcgattgcc    660
aaaggaattc ccgttttcgt atcggagtgc ggcggctcgg aagccaatgg cgacggacgg    720
ttaggcatag aagaatggaa aacctacgtc gattggatgg agagtcggaa aataagctgg    780
gtggcctggt ccgtttccga caagaacgaa accgcgtcca tgctgctccc ccgcgcctct    840
gccgatggca actggacgga agacctgctc aagccttggg gaaaactgac gcgtaattct    900
atccggaacg cgaatgatga aaacccggat atctga                              936
```

<210> SEQ ID NO 40
<211> LENGTH: 936
<212> TYPE: DNA
<213> ORGANISM: Artificial sequence
<220> FEATURE:
<223> OTHER INFORMATION: Nucleotide sequence representing double alanine substitutions made on SEQ ID N0: 3 wherein the codon for cysteine at positions 688 and 814 are replaced by alanine

<400> SEQUENCE: 40

```
gaaaacaaca ggaaaacgga ctaccgttcc atcgtagcgc agaacggccg tttacaggtg     60
atcggcacac aattgagcaa tgaaaaaggc gaacccgtcg tttacgggg agccagcctc    120 ggatggcaca acctctggcc ccgcttctat aacaagaacg cggtgcaatg gctggccgac    180
gattggaaat gcacggtcgt cagggctgca atgggcttgg aaattgaaga caactaccgg    240
gaaaatcccg aatttgcctt acagtgcatc acccctgtca tcgaatcggc tattgaaaac    300
ggaatctatg tgattatcga cttccacgca cacaacaaat acaccgaaga agccaaaaca    360
ttctttgccg ggatggccga aaaatacggg gaatatccga acgtgatcta tgaaatctgg    420
aacgaacccg attatttcga atgggaagaa gtaaaaacct attcggaaga agtgatcgcc    480
gtcatccgcg cgatcgaccc cgacaatatt atattggtcg gcagccccca ttgggaccag    540
gacctgcatc tggtagccga agacccgatc cgggatgtaa gcaacatcat gtacaccatg    600 cattttacg ccgcgaccca cgaggcctgg ctgcgtgacc ggaccgacga ggcgattgcc    660
aaaggaattc ccgttttcgt atcggaggcg ggcggctcgg aagccaatgg cgacggacgg    720
ttaggcatag aagaatggaa aacctacgtc gattggatgg agagtcggaa aataagctgg    780
gtggcctggt ccgtttccga caagaacgaa accgcgtcca tgctgctccc ccgcgcctct    840
gccgatggca actggacgga agacctgctc aagccttggg gaaaactgac gcgtaattct    900
atccggaacg cgaatgatga aaacccggat atctga                              936
```

<210> SEQ ID NO 41
<211> LENGTH: 936
<212> TYPE: DNA
<213> ORGANISM: Artificial sequence
<220> FEATURE:
<223> OTHER INFORMATION: Nucleotide sequence representing triple alanine substitutions made on SEQ ID N0: 3 wherein the codon for cysteine at positions 190, 265 and 688 are replaced by alanine

<400> SEQUENCE: 41

```
gaaaacaaca ggaaaacgga ctaccgttcc atcgtagcgc agaacggccg tttacaggtg      60
atcggcacac aattgagcaa tgaaaaaggc gaacccgtcg ttttacgggg agccagcctc     120
ggatggcaca acctctggcc ccgcttctat aacaagaacg cggtgcaatg gctggccgac     180
gattggaaag cgacggtcgt cagggctgca atgggcttgg aaattgaaga caactaccgg     240
gaaaatcccg aatttgcctt acaggcgatc acccctgtca tcgaatcggc tattgaaaac     300
ggaatctatg tgattatcga cttccacgca cacaacaaat acaccgaaga agccaaaaca     360
ttctttgccg ggatggccga aaaatacggg gaatatccga acgtgatcta tgaaatctgg     420
aacgaacccg attatttcga atgggaagaa gtaaaaacct attcggaaga agtgatcgcc     480
gtcatccgcg cgatcgaccc cgacaatatt atattggtcg gcagccccca ttgggaccag     540
gacctgcatc tggtagccga agacccgatc cgggatgtaa gcaacatcat gtacaccatg     600 cattttacg ccgcgaccca cgaggcctgg ctgcgtgacc ggaccgacga ggcgattgcc     660
aaaggaattc ccgttttcgt atcggaggcg ggcggctcgg aagccaatgg cgacggacgg     720
ttaggcatag aagaatggaa aacctacgtc gattggatgg agagtcggaa ataagctgg      780 gtggcctggt ccgtttccga caagaacgaa acctgctcca tgctgctccc ccgcgcctct     840
gccgatggca actggacgga agacctgctc aagccttggg gaaaactgac gcgtaattct     900
atccggaacg cgaatgatga aaacccggat atctga                              936
```

<210> SEQ ID NO 42
<211> LENGTH: 936
<212> TYPE: DNA
<213> ORGANISM: Artificial sequence
<220> FEATURE:
<223> OTHER INFORMATION: Nucleotide sequence representing triple alanine
substitutions made on SEQ ID NO: 3 wherein the codon for cysteine
at positions 190, 688 and 814 are replaced by alanine

<400> SEQUENCE: 42

```
gaaaacaaca ggaaaacgga ctaccgttcc atcgtagcgc agaacggccg tttacaggtg      60
atcggcacac aattgagcaa tgaaaaaggc gaacccgtcg ttttacgggg agccagcctc     120
ggatggcaca acctctggcc ccgcttctat aacaagaacg cggtgcaatg gctggccgac     180
gattggaaag cgacggtcgt cagggctgca atgggcttgg aaattgaaga caactaccgg     240
gaaaatcccg aatttgcctt acagtgcatc acccctgtca tcgaatcggc tattgaaaac     300
ggaatctatg tgattatcga cttccacgca cacaacaaat acaccgaaga agccaaaaca     360
ttctttgccg ggatggccga aaaatacggg gaatatccga acgtgatcta tgaaatctgg     420
aacgaacccg attatttcga atgggaagaa gtaaaaacct attcggaaga agtgatcgcc     480
gtcatccgcg cgatcgaccc cgacaatatt atattggtcg gcagccccca ttgggaccag     540
gacctgcatc tggtagccga agacccgatc cgggatgtaa gcaacatcat gtacaccatg     600 cattttacg ccgcgaccca cgaggcctgg ctgcgtgacc ggaccgacga ggcgattgcc     660
aaaggaattc ccgttttcgt atcggaggcg ggcggctcgg aagccaatgg cgacggacgg     720
ttaggcatag aagaatggaa aacctacgtc gattggatgg agagtcggaa ataagctgg      780 gtggcctggt ccgtttccga caagaacgaa accgcgtcca tgctgctccc ccgcgcctct     840
gccgatggca actggacgga agacctgctc aagccttggg gaaaactgac gcgtaattct     900
atccggaacg cgaatgatga aaacccggat atctga                              936
```

<210> SEQ ID NO 43
<211> LENGTH: 936

<212> TYPE: DNA
<213> ORGANISM: Artificial Sequence
<220> FEATURE:
<223> OTHER INFORMATION: Nucleotide sequence representing triple alanine
      substitutions made on SEQ ID N0: 3 wherein the codon for cysteine
      at positions 265, 688 and 814 are replaced by alanine

<400> SEQUENCE: 43

```
gaaaacaaca ggaaaacgga ctaccgttcc atcgtagcgc agaacggccg tttacaggtg    60
atcggcacac aattgagcaa tgaaaaaggc gaacccgtcg ttttacgggg agccagcctc   120
ggatggcaca acctctggcc ccgcttctat aacaagaacg cggtgcaatg gctggccgac   180
gattggaaat gcacggtcgt cagggctgca atgggcttgg aaattgaaga caactaccgg   240
gaaaatcccg aatttgcctt acaggcgatc acccctgtca tcgaatcggc tattgaaaac   300
ggaatctatg tgattatcga cttccacgca cacaacaaat acaccgaaga agccaaaaca   360
ttctttgccg ggatggccga aaaatacggg gaatatccga acgtgatcta tgaaatctgg   420
aacgaacccg attatttcga atgggaagaa gtaaaaacct attcggaaga agtgatcgcc   480
gtcatccgcg cgatcgaccc cgacaatatt atattggtcg gcagcccccca ttgggaccag   540
gacctgcatc tggtagccga agacccgatc cgggatgtaa gcaacatcat gtacaccatg   600
cattttacg ccgcgaccca cgaggcctgg ctgcgtgacc ggaccgacga ggcgattgcc   660
aaaggaattc ccgttttcgt atcggaggcg ggcggctcgg aagccaatgg cgacggacgg   720
ttaggcatag aagaatggaa aacctacgtc gattggatgg agagtcggaa aataagctgg   780
gtggcctggt ccgtttccga caagaacgaa accgcgtcca tgctgctccc ccgcgcctct   840
gccgatggca actggacgga agacctgctc aagccttggg gaaaactgac gcgtaattct   900
atccggaacg cgaatgatga aaacccggat atctga                             936
```

<210> SEQ ID NO 44
<211> LENGTH: 936
<212> TYPE: DNA
<213> ORGANISM: Artificial sequence
<220> FEATURE:
<223> OTHER INFORMATION: Nucleotide sequence representing triple alanine
      substitutions made on SEQ ID N0: 3 wherein the codon for cysteine
      at positions 190, 265 and 814 are replaced by alanine

<400> SEQUENCE: 44

```
gaaaacaaca ggaaaacgga ctaccgttcc atcgtagcgc agaacggccg tttacaggtg    60
atcggcacac aattgagcaa tgaaaaaggc gaacccgtcg ttttacgggg agccagcctc   120
ggatggcaca acctctggcc ccgcttctat aacaagaacg cggtgcaatg gctggccgac   180
gattggaaag cgacggtcgt cagggctgca atgggcttgg aaattgaaga caactaccgg   240
gaaaatcccg aatttgcctt acaggcgatc acccctgtca tcgaatcggc tattgaaaac   300
ggaatctatg tgattatcga cttccacgca cacaacaaat acaccgaaga agccaaaaca   360
ttctttgccg ggatggccga aaaatacggg gaatatccga acgtgatcta tgaaatctgg   420
aacgaacccg attatttcga atgggaagaa gtaaaaacct attcggaaga agtgatcgcc   480
gtcatccgcg cgatcgaccc cgacaatatt atattggtcg gcagcccccca ttgggaccag   540
gacctgcatc tggtagccga agacccgatc cgggatgtaa gcaacatcat gtacaccatg   600
cattttacg ccgcgaccca cgaggcctgg ctgcgtgacc ggaccgacga ggcgattgcc   660
aaaggaattc ccgttttcgt atcggagtgc ggcggctcgg aagccaatgg cgacggacgg   720
ttaggcatag aagaatggaa aacctacgtc gattggatgg agagtcggaa aataagctgg   780
```

```
gtggcctggt ccgtttccga caagaacgaa accgcgtcca tgctgctccc ccgcgcctct    840
gccgatggca actggacgga agacctgctc aagccttggg gaaaactgac gcgtaattct    900
atccggaacg cgaatgatga aaacccggat atctga                              936
```

<210> SEQ ID NO 45
<211> LENGTH: 936
<212> TYPE: DNA
<213> ORGANISM: Artificial sequence
<220> FEATURE:
<223> OTHER INFORMATION: Nucleotide sequence representing quadruple
      alanine substitutions made on SEQ ID NO: 3 wherein the codon for
      cysteine at positions 190, 265, 688 and 814 are replaced by
      alanine

<400> SEQUENCE: 45

```
gaaaacaaca ggaaaacgga ctaccgttcc atcgtagcgc agaacggccg tttacaggtg     60
atcggcacac aattgagcaa tgaaaaaggc gaacccgtcg ttttacgggg agccagcctc    120
ggatggcaca acctctggcc ccgcttctat aacaagaacg cggtgcaatg gctggccgac    180
gattggaaag cgacggtcgt cagggctgca atgggcttgg aaattgaaga caactaccgg    240
gaaaatcccg aatttgcctt acaggcgatc accccctgtca tcgaatcggc tattgaaaac    300
ggaatctatg tgattatcga cttccacgca cacaacaaat acaccgaaga agccaaaaca    360
ttctttgccg ggatggccga aaaatacggg gaatatccga acgtgatcta tgaaatctgg    420
aacgaacccg attatttcga atgggaagaa gtaaaaacct attcggaaga agtgatcgcc    480
gtcatccgcg cgatcgaccc cgacaatatt atattggtcg gcagccccca ttgggaccag    540
gacctgcatc tggtagccga agacccgatc cgggatgtaa gcaacatcat gtacaccatg    600
catttttacg ccgcgaccca cgaggcctgg ctgcgtgacc ggaccgacga ggcgattgcc    660
aaaggaattc ccgttttcgt atcggaggcg ggcggctcgg aagccaatgg cgacggacgg    720
ttaggcatag aagaatggaa aacctacgtc gattggatgg agagtcggaa aataagctgg    780
gtggcctggt ccgtttccga caagaacgaa accgcgtcca tgctgctccc ccgcgcctct    840
gccgatggca actggacgga agacctgctc aagccttggg gaaaactgac gcgtaattct    900
atccggaacg cgaatgatga aaacccggat atctga                              936
```

CELLULASE DERIVED FROM METAGENOMICS

CROSS REFERENCES TO RELATED APPLICATIONS

This application is a national-stage entry under 35 U.S.C. § 371 of International Application PCT/IN2016/050395 designating the United States, filed Nov. 11, 2016, which international application claims the benefit of priority to Indian Patent Application 3690/DEL/2015, filed Nov. 12, 2015.

FIELD OF THE INVENTION

The present invention provides a novel endoglucanase gene (GH5 family) from the soil metagenome. More specifically, this invention provides a recombinant plasmid and the recombinant hosts for the expression of novel gene sequence having cellulase activity. The cellulase in the invention has high specific activity towards β-1,4 linkages in substrates such as carboxy-methyl cellulose and barley-β-glucan etc. This novel cellulase can have many industrial applications eg. food and feed industry, detergent, textile and biofuel industry etc.

BACKGROUND OF THE INVENTION

The increasing demand on the one hand and depleting fossil fuels on the other, as energy sources has necessitated the development of alternative sources of energy. The production of renewable biofuels using naturally abundant lignocellulosic biomass such as agricultural waste, forestry waste and municipal waste will reduce society's dependence on fossil fuels. Cellulose being the major component of lignocellulose, the need for novel and highly efficient cellulases have been realized enormously (Xing et al., 2012).

Cellulases find their use in versatile industrial applications such as in paper industry for deinking of recycled paper, textile industry for biopolishing of fabric and reducing harshness of cotton cloth, laundry industry as an additive to detergents, food and feed industry to improve the digestibility of food, brewing industry and agricultural industry for bioprocessing of crops and many other applications (Bhat, 2000; Xing et al., 2012).

Cellulases belong to glycosyl hydrolase family of enzymes which catalyse cellulolysis in a concerted manner. Endoglucanase (EC 3.2.1.4) randomly cleaves the internal 1,4-β-D-glucan linkage, producing free ends. Exoglucanase (EC 3.2.1.91 and 3.2.1.176) progressively act on reducing and non-reducing ends to release cellobiose. The di-ssacharide produced is then digested by β-glucosidases (EC 3.2.1.21) to release free glucose. These enzymes work synergistically to bring the cellulose hydrolysis (Aubert et al., 1988; Lynd et al., 2002). Endoglucanases are the major enzymes to initiate and bring out extensive hydrolysis of internal linkages. Endoglucanases fall into 14 families of glycosyl hydrolase families, according to the classification by Carbohydrate Active Enzymes database (Lombard et al., 2014)

One of the approaches to discover novel cellulases is through metagenomics which is a culture-independent approach for studying the microbial diversity and exploring novel enzymes of industrial importance (Handelsman, 2004; Zengler et al., 2002).

Among the various natural environments, soil is the most diverse and challenging with respect to the microbiota present in it (Daniel, 2005). Many novel industrially relevant enzymes, like cellulases, amylases, lipases, proteases, xylanases etc. have been discovered from soil metagenomics (Daniel, 2005; Xing et al., 2012). Several of these enzymes have far superior properties w.r.t. activity, specificity, stability etc. than the known enzymes.

Many cellulases have been derived from the metagenomic studies, which have remarkable properties, like thermostability, halostability, pH stability. As examples, novel metagenomic GH5 cellulases have been isolated from ruminal fluid of cow which is active against wide range of substrates (Ko et al., 2013). A thermophillic GH9 endoglucanase having the optimal activity at 75° C. have been isolated from sugarcane bagasse (Kanokratana et al., 2014). A metagenome derived GH12 cellulase isolated from leaf branch compost has the optimum temperature of 90° C. (Okano et al., 2014). The cellulases isolated from rumen of cattle have specific activity ranging from 6-70 U/mg on CMC as substrate (Ferrer et al., 2008). Such properties, associated with newer proteins having industrial relevance is a great need for the full and successful aim of harvesting biomass as sources of affordable and green energy.

Therefore it is an object of the present invention to provide cellulases which are active at high temperature, over wide pH range, broad stability and tolerance to a range of chemical and physical conditions, high activity in the presence of salts and chemicals etc.

It explains the complete contig of the metagenomic clone isolated from metagenomic library showing the presence of different open reading frames (ORFs).

Figure 1:
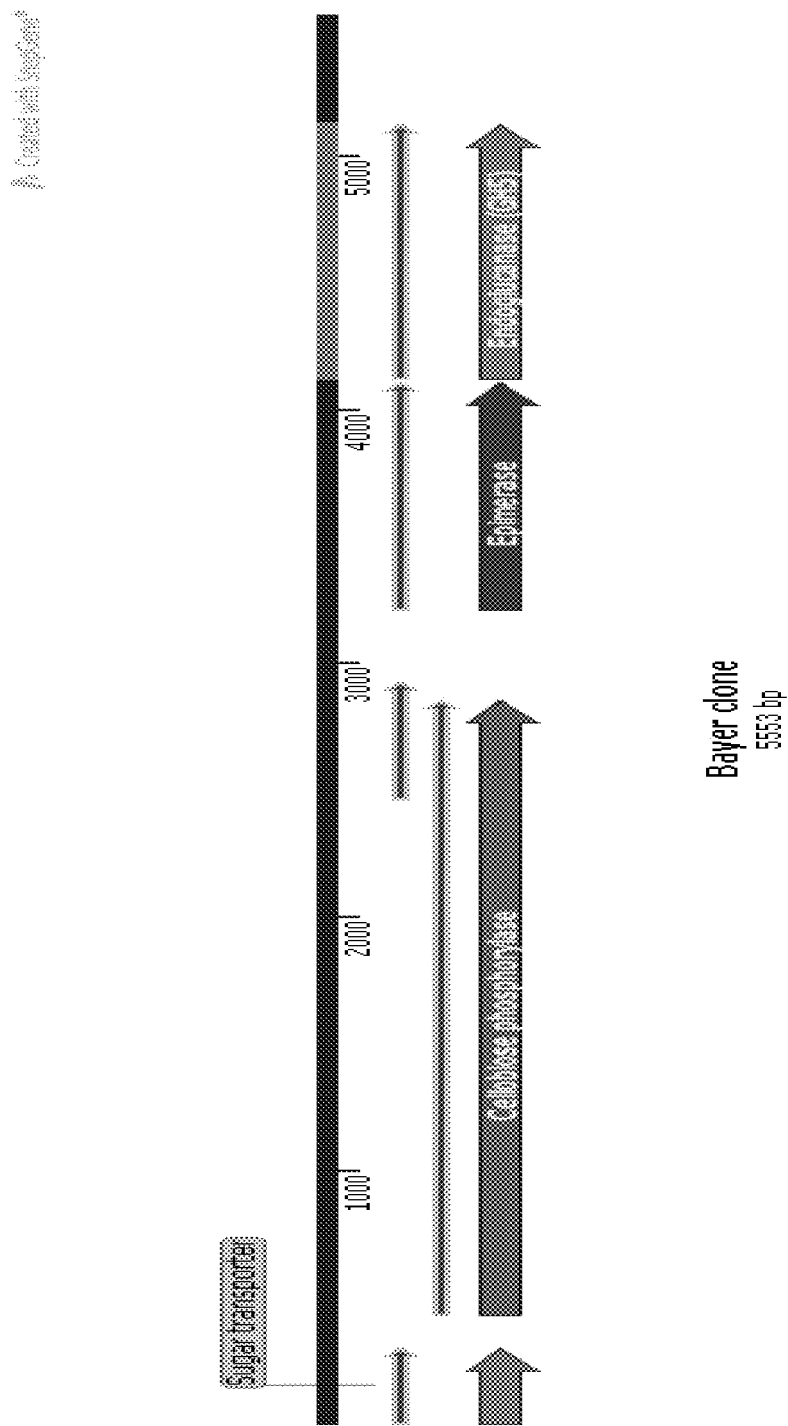
FIG. 1: The sequencing of positive clone from plasmid library revealed the gene cluster with 5553 bases consisting of several open reading frames.
Figure 2:
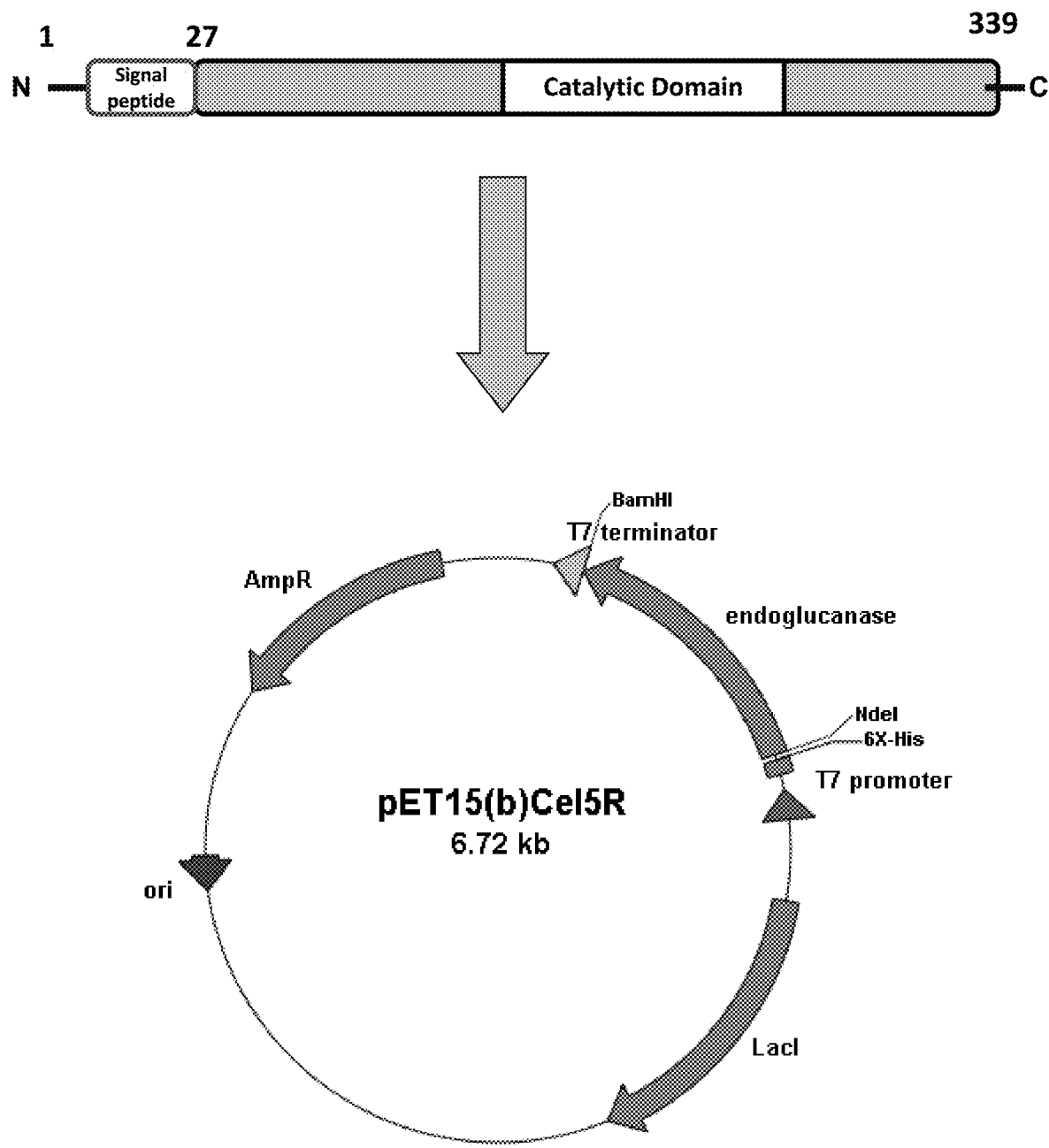
Figure 3A:
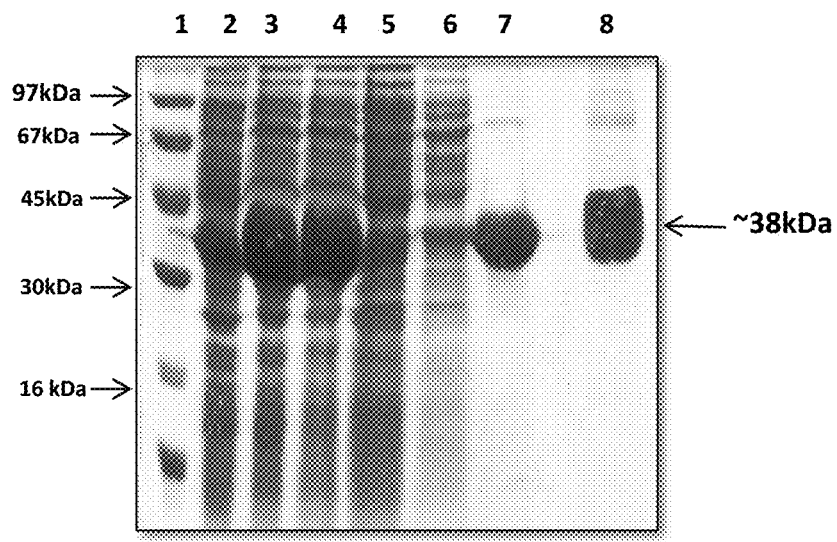
Figure 3B:
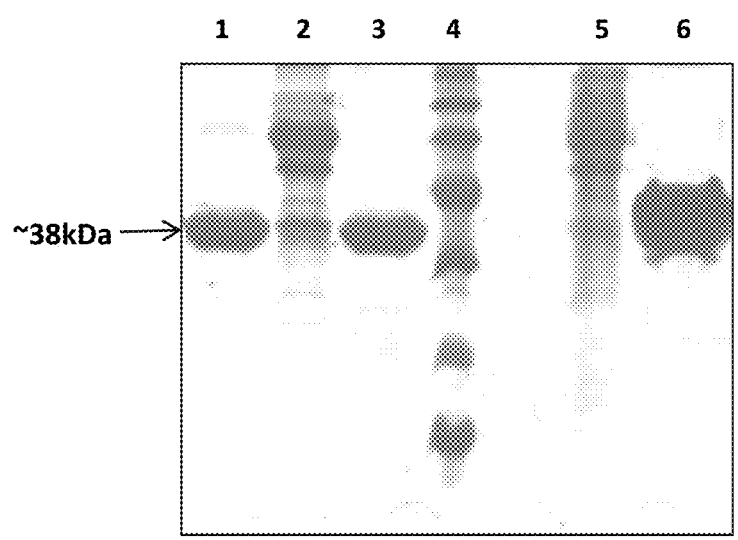
Figure 3C:
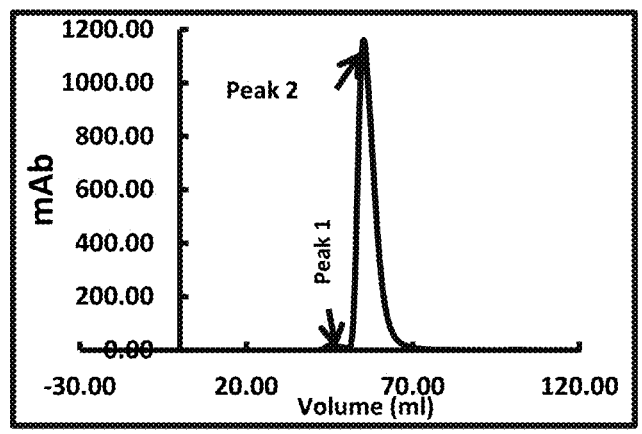
Figure 3D:
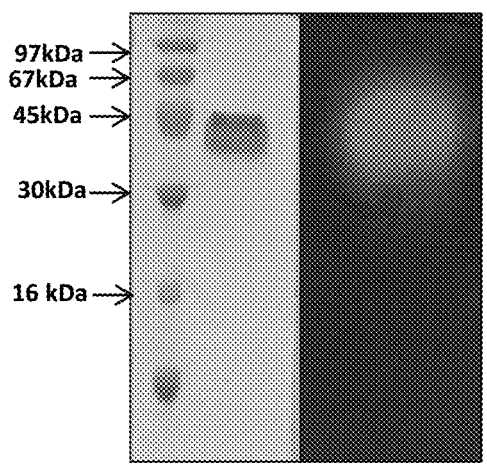

FIG. 2: The schematic diagram showing cellulase gene and the recombinant vector containing the cellulase gene.

It explains the schematic of cloning of the novel gene SEQ ID NO: 1 in pET15(b) vector with N-terminal 6×-His-tag FIGS. 3A-3D: 10% SDS gel showing expression and purification profile of the cellulase gene by Ni-NTA and Superdex-75 gel filtration chromatography in E. Coli Rosetta DE3 cells.

It explains the expression and purification profile of endoglucanase. (FIG. 3A) 10% SDS-PAGE showing expressed and Ni-NTA purified endoglucanase. Lane 1: protein molecular weight marker; lane 2: crude cell lysate of uninduced E. coli. BL21(DE3) Rosetta cells harboring pET15(b)-Cel5R; Lane 3: crude lysate of E. coli. BL21 (DE3) Rosetta cells harbouring pET15(b)-Cel5R induced with 1 mM IPTG; Lane 4: Supernatant from cell lysate after centrifugation, loaded onto Ni-NTA beads; lane 5: Flow through; lane 6: wash with 30 mM imidazole; lane 7: elute with 300 mM imidazole run in reducing conditions; dye; lane 8: elute with 300 mM imidazole run in non-reducing condition. (FIG. 3B) 10% SDS-PAGE profile of gel filtration on Superdex-75 (16/60). Lane 1: Ni$^{+2}$-NTA purified protein; lane 2: Peak-1 in reducing condition; lane 3: Peak-2 in reducing condition; lane 4: Protein molecular weight marker; lane 5: Peak-1 in non-reducing condition; lane 6: Peak-2 in non-reducing condition (FIG. 3C) Superdex-75 gel Filtration chromatography profile showing Peak 1 and Peak 2 by arrowhead. (FIG. 3D) Plate CMC zymogram (0.5% Agarose+0.5% CMC) showing cellulase activity band.

Figure 4A:
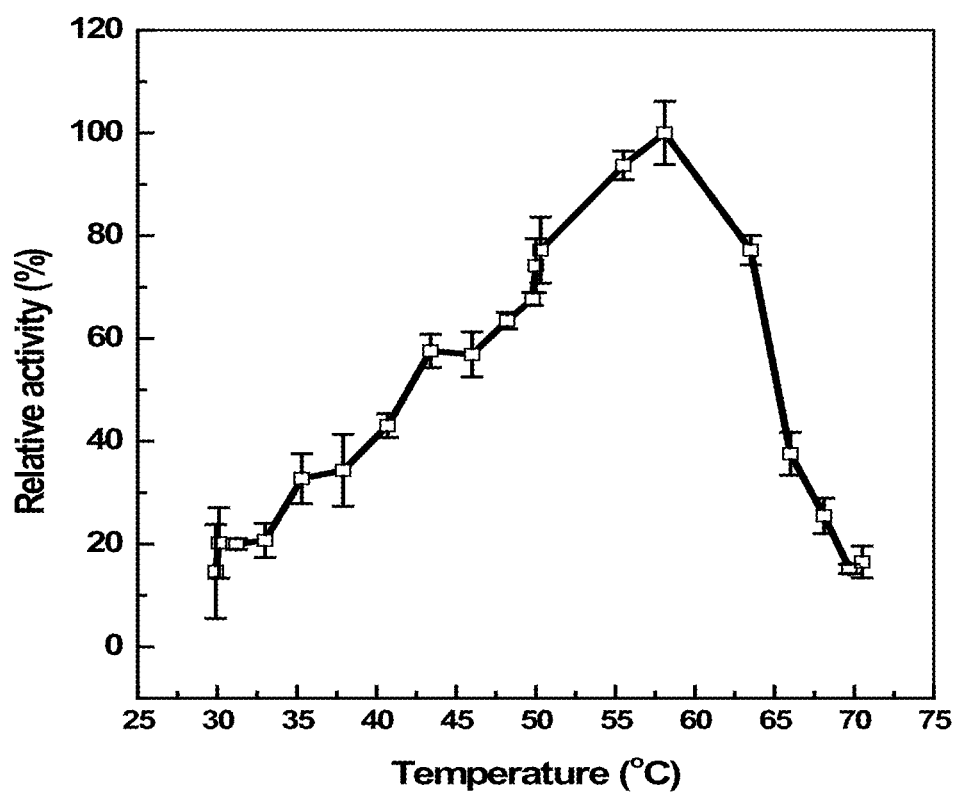

FIG. 4A: Temperature optima of the novel cellulase polypeptide showing the maximum activity at 58° C.

It explains the determination of optimum temperature for recombinant endoglucanase activity. Activity was measured at pH 6.0 (sodium-citrate buffer) at the indicated temperatures for 15 min.

Figure 4B:
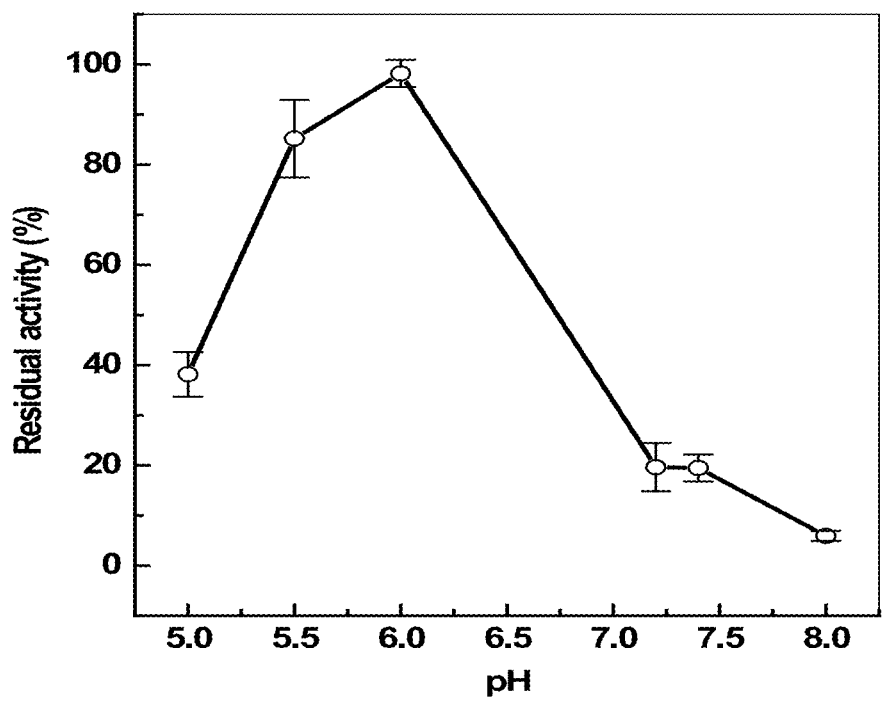

FIG. 4B: pH optima profile of the cellulase activity showing the maximum activity at pH-6, sodium citrate buffer.

It explains the determination of optimum pH for recombinant endoglucanase activity. Enzyme assays were performed at indicated pH at 58° C. for 15 min.

Figure 4C:
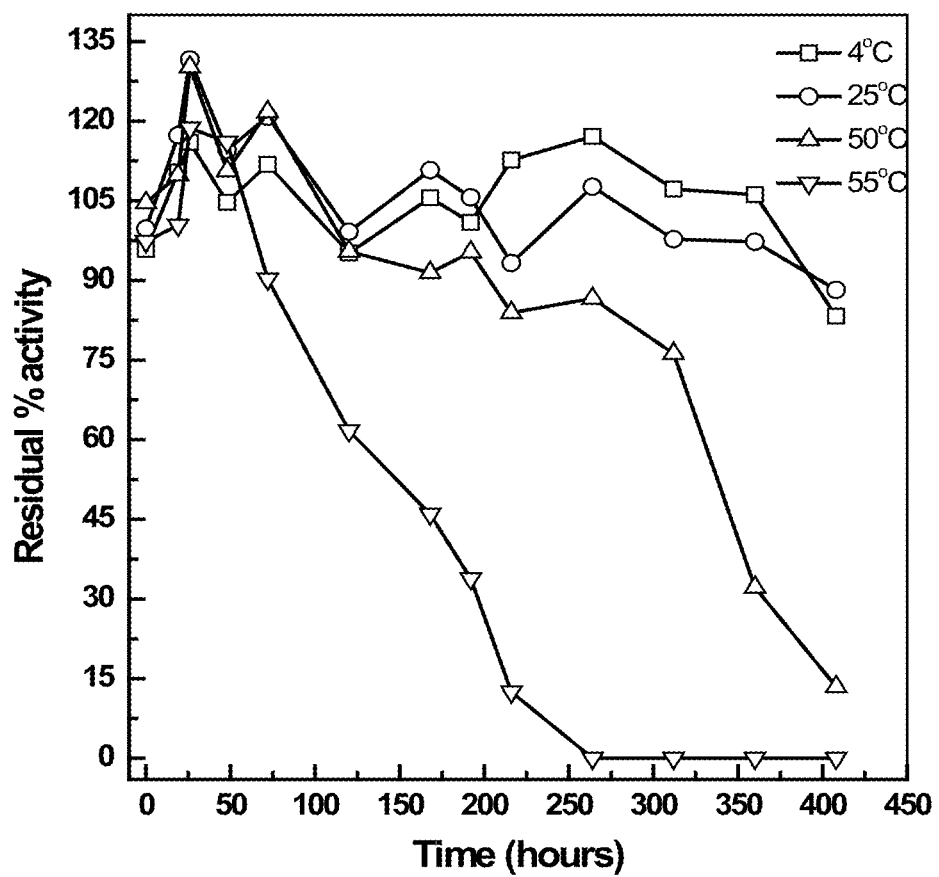

FIG. 4C: Graph depicting the stability of the cellulase at different temperatures (4, 25, 50, 55° C.)

It explains the thermal stability of the recombinant endoglucanase. Activity was measured under optimal condition (sodium-citrate buffer of pH 6.0, 58° C., 15 min) after incubation of the enzyme at indicated temperatures for different time intervals.

Figure 4D:
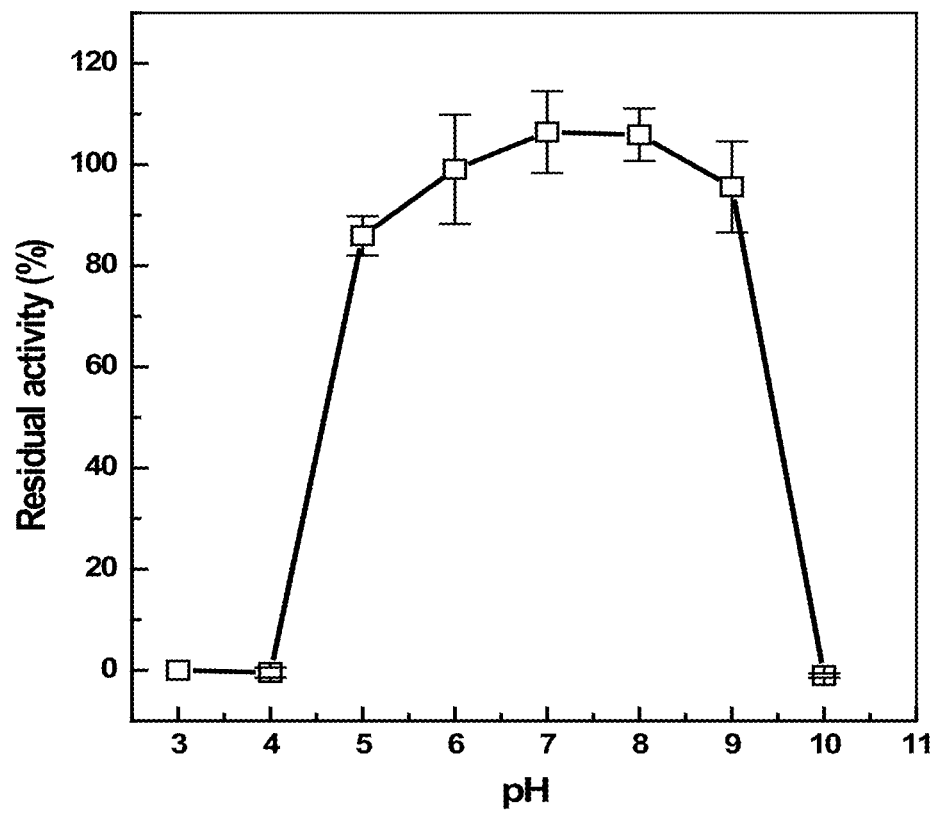

FIG. 4D: Profile showing the stability of the cellulase at different pH after incubations for 7 days at 25° C.

It explains the pH stability of the recombinant endoglucanase. Activity was measured under optimal condition (sodium-citrate buffer of pH 6.0, 58° C., 15 min) after the purified enzyme was incubated in buffers (0.1M Na-citrate buffer, pH 4.0-6.0; 0.1 M Tris-HCl buffer, pH 7.0-8.0; 0.1 M glycine-NaOH buffer, pH 9-10.0) at 25° C. for 168 h.

Figure 4E:
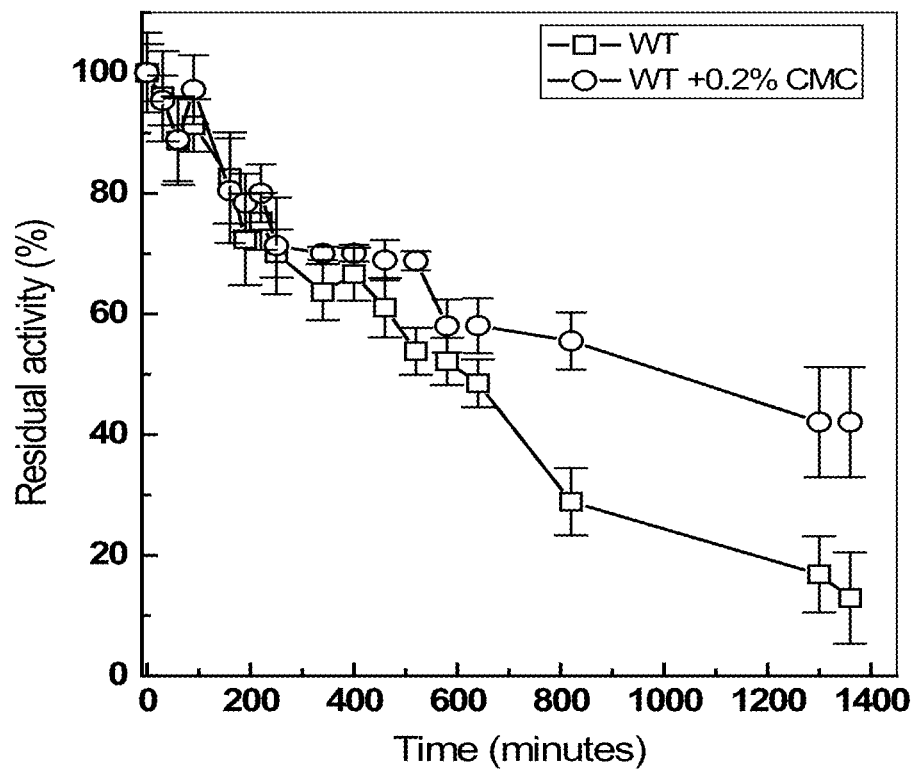

FIG. 4E: profile showing the stability at 58° C. when cellulase polypeptide was incubated in the presence of 0.2% CMC substrate versus without it.

It explains the relative thermal stability at 58° C. in the presence of 0.2% CMC versus without substrate. Activity was measured under optimal condition (sodium-citrate buffer of pH 6.0, 58° C., 15 min) after incubation of the enzyme for different time intervals.

Figure 5:
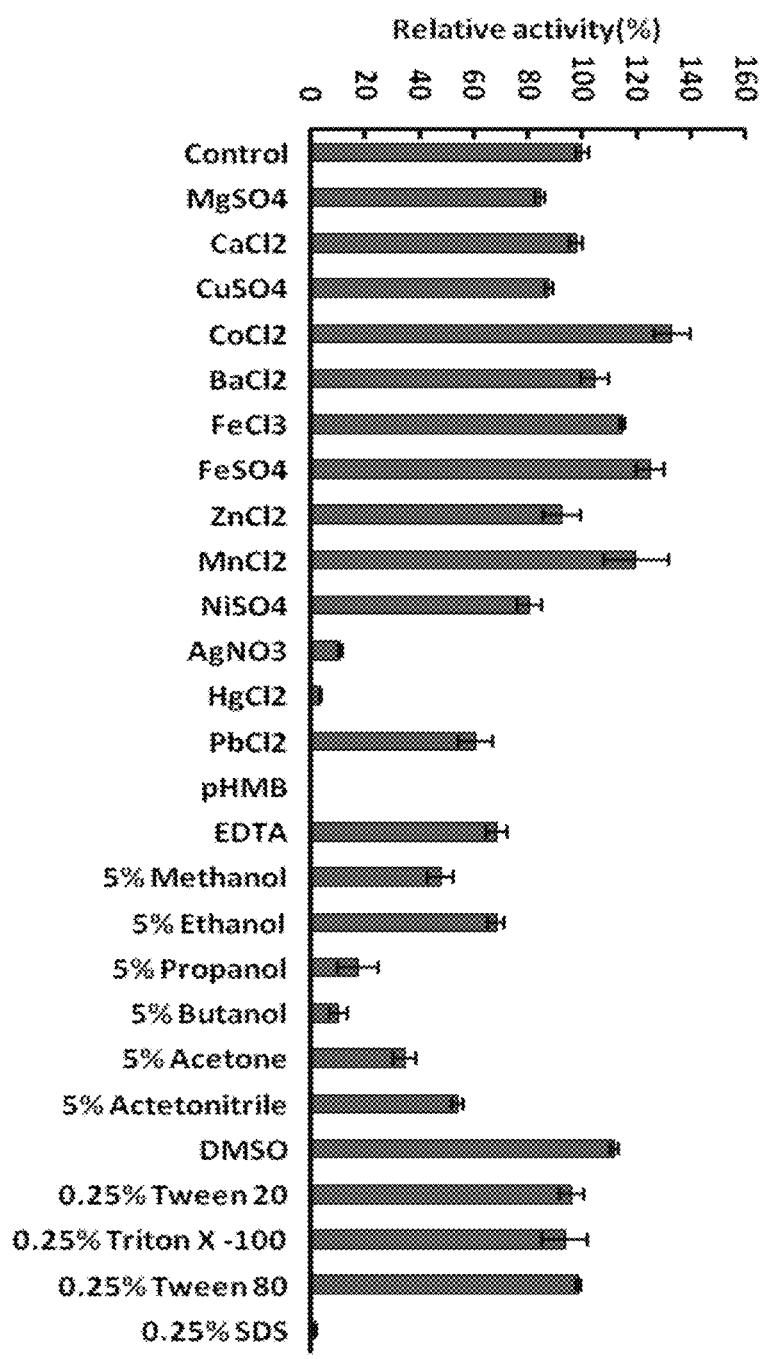

FIG. 5: cellulase activity in the presence of different salts, organic solvents and detergents It explains the relative activity of recombinant endoglucanase in the presence of various metal ions at 1 mM concentration, organic solvents at 5% concentration, and detergents at 0.25% in reaction. Activity was measured under optimal condition (sodium-citrate buffer of pH 6.0, 58° C., 15 min).

Figure 6A:
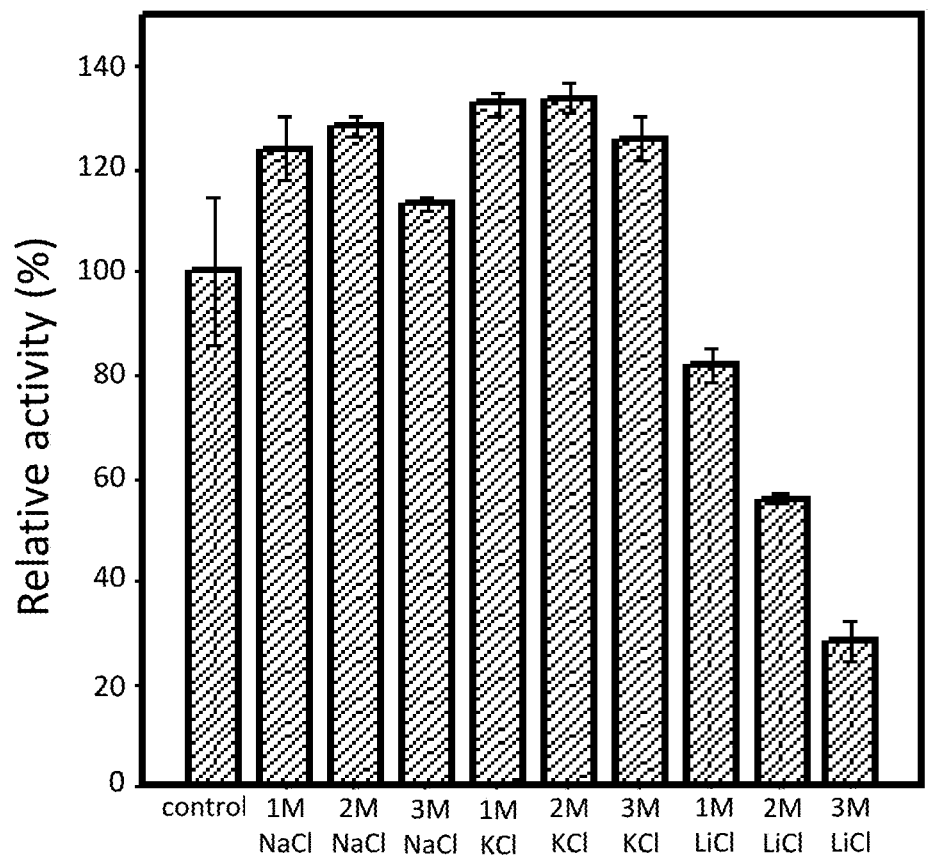

FIG. 6A: Graph showing the activation of enzyme in the presence of different salts like NaCl, KCl, LiCl.

Figure 6B:
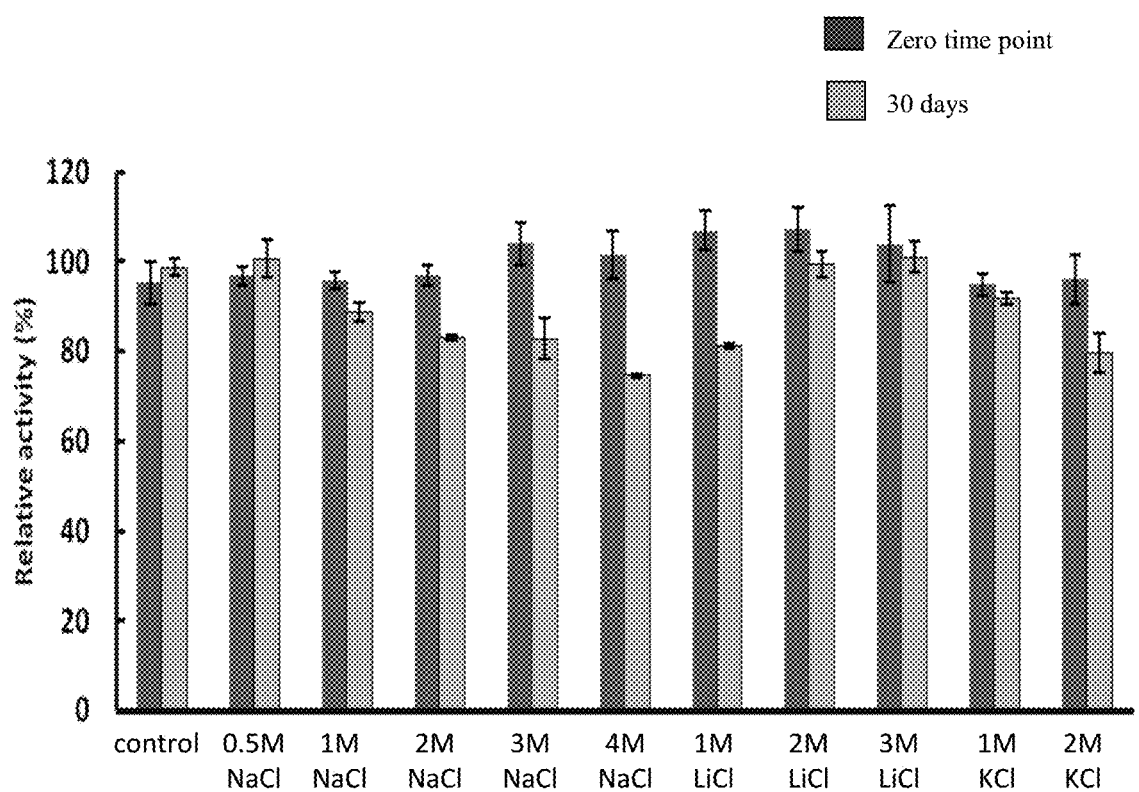

It shows relative effect of various concentrations of ionic salts (NaCl, LiCl, KCl) on the activity of recombinant endoglucanase FIG. 6B: Graph depicting the stability of cellulase in the presence of different salts on incubation for 30 days.

It explains the residual relative activity of endoglucanase on incubation in various salts indicating halotolerance. Activity was measured under optimal condition (sodium-citrate buffer of pH 6.0, 58° C., 15 min) after incubation for 30 days at 25° C.

OBJECT OF THE INVENTION

The main object of the invention is to provide a novel metagenome derived nucleotide sequence having SEQ ID NO: 3 and SEQ ID NO: 31-45 having cellulase activity.

It is another object of the invention to provide the amino acid sequence with SEQ ID NO: 2 encoded by the gene with nucleotide SEQ ID NO: 1 having an upstream hydrophobic region.

Yet another aspect of the present invention is to provide a polynucleotide having at least 85% identity to a polynucleotide SEQ ID NO: 1.

Yet another aspect of the present invention is to provide a polypeptide having at least 85% identity to a polypeptide SEQ ID NO: 2.

It is an object of the invention to provide the recombinant vectors harboring the novel gene from the metagenomic library.

Still another aspect of the present invention provides an expression vector encoding a polynucleotide having at least 85% identity to a polynucleotide sequence SEQ ID NO: 1.

Still another aspect of the present invention provides an expression vector encoding a polypeptide having at least 85% identity to a polypeptide sequence SEQ ID NO: 2.

It is a further object of this invention to provide the recombinant hosts containing the recombinant vector for the expression of the novel gene with SEQ ID NO: 1

It is another object of this invention to provide a process for the expression of polypeptides from metagenomic derive gene with SEQ ID NO: 1 in $E.\ coli$.

It is another object of the invention to provide truncated gene sequence and the corresponding polypeptide with SEQ ID NO: 3 and SEQ ID NO: 4 respectively obtained by deleting the N-terminal region of polypeptide with SEQ ID NO: 2.

It is the object of the invention to provide the nucleotide sequence of the functional derivatives of the SEQ ID NO: 3 obtained by site-directed mutagenesis, designated from SEQ ID NO: 31 to SEQ ID NO: 45.

It is the object of the invention to provide the functional derivatives of the polypeptide sequence with SEQ ID NO: 4 obtained by site-directed mutagenesis expressing the active and stable cellulase protein and designated from SEQ ID NO 5 to SEQ ID NO 19.

It is the further object of the invention to provide a process for the production of active enzyme from the recombinant hosts.

It is another object of the invention to provide the process for purification and refolding of the bioactive cellulase protein from the expression hosts.

It is the another object of the invention to provide the gene sequences and the corresponding polypeptides with one or more amino acid mutated and their recombinant vectors and hosts expressing the active enzyme forms.

SUMMARY OF THE INVENTION

Accordingly, the present invention provides a novel metagenome derived nucleotide sequence having SEQ ID NO: 1, SEQ ID NO: 3 and SEQ ID NO: 31-45 having cellulase activity.

In an embodiment the invention provides the corresponding polypeptide sequence is selected from the group consisting of SEQ ID NO: 2, SEQ ID NO: 4 and SEQ ID NO: 5-19.

In an embodiment the invention provides recombinant vectors comprising of the nucleotide sequence id no. 3 wherein the vector is selected from the group comprising of $E.\ coli$ expression vector, a yeast expression vector, filamentous fungal expression vector, and insect or animal cell vector.

In an embodiment the invention provides the polypeptide, wherein the polypeptide is having high specific activity towards β-1, 4 linkages in substrates selected from group consisting of Carboxy-methyl cellulose and Barley-β-glucan.

In another embodiment the invention provides the expression vector, wherein the expression vector comprises a polynucleotide having at least 85% identity to a polynucleotide sequence selected from the group consisting of SEQ ID NO: 1, SEQ ID NO: 3 and SEQ ID NO: 31-45.

In an embodiment the invention provides the expression vector, wherein the expression vector encodes a polypeptide having at least 85% identity to a polypeptide sequence selected from the group consisting of SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and SEQ ID NO: 19.

In an embodiment the invention provides the host cell expressing the recombinant vector wherein the host cell is selected from the group comprising of *E. coli*, yeast cells, *Bacillus subtilis*, *Aspergillus niger*, and insect or animal host.

In an embodiment the invention provides a method for producing metagenome derived polypeptide having amino acid sequence selected from the group consisting of SEQ ID NO: 2, 4 and 5-19 comprising the steps:
a. isolating soil metagenomic DNA;
b. constructing library of the metagenomic DNA obtained in step (a);
c. screening the library obtained in step (b) for positive clones having endoglucanase activity using 0.5% CMC as substrate;
d. sequencing the positive clones obtained in step (c) to identify ORF encoding cellulase gene having SEQ ID NO: 1;
e. performing PCR of the ORF encoding cellulase gene identified in step (d) using primers having SEQ ID NO: 20 and SEQ ID NO: 21 to amplify the gene fragment;
f. cloning the amplified gene fragment obtained in step (e) into recombinant vector pET15b-Cel5R;
g. transforming the recombinant vector of step (f) into expression host BL21-DE3;
h. repeating the steps (e) to (g) using primers having SEQ ID NO:20, SEQ ID NO: 22 to obtain truncated gene sequence with SEQ ID NO: 3 and corresponding polypeptide with SEQ ID NO: 4;
i. performing cysteine to alanine mutation on polypeptide having SEQ ID NO: 4 using primers having SEQ ID NO: 23 to 30 to obtain amplified mutated DNA fragment having SEQ ID NO: 31-45;
j. confirming the sequence of mutated DNA obtained in step (i) by sequencing;
k. isolating, cloning and transforming the mutated DNA of step (i) into Rosetta (BL21) cells;
l. checking the expression of the clone harbouring mutated polypeptide on 10% SDS;
m. purifying the expressed variant polypeptide obtained in step (1) to homogeneity by using the combinations of different chromatography's to obtain the protein product.

In an embodiment the invention provides use of the polypeptide for decreasing the amount of beta-glucans in bakery industry.

In an embodiment the invention provides use of the polypeptide for increasing the digestibility of feed in food and feed industry.

In an embodiment the invention provides use of the polypeptide for reducing the roughness of fabrics in textile industry.

The present invention provides the amino acid sequence having SEQ ID NO: 2 of the nucleic acid encoding the cellulase gene having SEQ ID NO: 1 which belongs to the Glycosyl Hydrolase family 5, and has endoglucanase activity. The present invention also provides the truncated and modified derivatives of the original sequence with SEQ ID NO: 1 obtained from the original sequence but exhibits high cellulase activity with SEQ ID NO: 3.

The present invention provides the polypeptide sequence of truncated cellulase gene with SEQ ID NO: 4 which expresses highly active endoglucanase gene.

Another embodiment is to provide the nucleotide sequences with SEQ ID NO: 3 and its mutated derivatives thereof with SEQ ID NO: 31 to SEQ ID NO: 45.

The present invention also provides the polypeptide sequences with SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19 which are obtained by substitution of one or more amino acids from SEQ ID NO: 4.

The present invention also provides an expression vector encoding a polynucleotide having at least 85% identity to a polynucleotide sequence SEQ ID NO: 1 and SEQ ID NO: 3.

The present invention also provides an expression vector encoding a polypeptide having at least 85% identity to a polypeptide sequence SEQ ID NO: 2 and SEQ ID NO: 4.

The present invention provides recombinant vectors and the recombinant microorganisms expressing the cellulase gene with SEQ ID NO: 1, SEQ ID NO: 3 with and without N-terminal or C-terminal 6X-His tag to aid in purification.

The invention also provides a process for the enhanced expression of cellulase gene from the recombinant host harboring the cellulase gene with gene SEQ ID NO: 1, SEQ ID NO: 3.

The present invention also provides a process for optimized refolding of the protein expressed from the recombinant host containing the gene SEQ ID NO: 3.

The present invention also provides a process for obtaining homogenous cellulase protein from the recombinant microorganism expressing the cellulase gene with polypeptide sequence of SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19.

The present invention also provides a novel cellulase gene and its functional derivatives which exhibits high temperature optima, wide pH range, extreme temperature and pH stability.

In one aspect, the enzyme of the present invention also exhibits enhanced activity in the presence of salts and also very stable in the presence of high concentrations of salts. In another aspect, the enzymes of invention have endoglucanase activity that is used to generate glucans from 1,4-β- and 1,3-β-glucoside linkages in polysaccharides such as carboxy-methyl cellulose and barley-β-glucan linkages.

In another aspect, the cellulase can be used in bakery industry to decrease the amount of beta-glucans, and the food and feed industry to increase the digestibility of feed, and in the textile industry for reducing the roughness of fabrics and various other industrial applications.

DETAILED DESCRIPTION OF THE INVENTION

The invention is based on the discovery of the novel gene sequence with SEQ ID NO: 1 derived from one of the most diverse and versatile habitats of the ecosystem, more preferably soil habitat from forest.

In the present invention, the procedure for plasmid metagenomic library construction from the DNA isolated from IMTech forest soil was followed using the commercial UltraClean™ and PowerMax™ kits (Mo Bio Laboratories Inc., Carlsbad, Calif., USA). The soil DNA was cloned in pEZSeq vector between EcoRI and HindIII restriction sites. The clones were screened on Luria-Bertani agar plate supplemented with 0.5% carboxymethyl cellulose and stained using congo red dye.

In the present invention, positive clones showing cellulase activity were sequenced. One of the novel ORFs having the size of 1017 bp was then sub-cloned. In the present invention, the ORF encoded a 338 amino acid polypeptide which was only about 65% identical to the already existing cellulase as seen by National Center for Biotechnology Information blastp search.

The present invention shows a new cellulase with improved properties. Therefore the present invention relates in its first embodiment to the polypeptide having the amino acid sequence with SEQ ID NO: 2 and a functional polypeptide thereof with SEQ ID NO: 4 which is obtained by truncation of N-terminal hydrophobic patch from SEQ ID NO. 2.

Another embodiment is to provide the nucleotide sequences with SEQ ID NO: 3 and its mutated derivatives thereof with SEQ ID NO: 31 to SEQ ID NO: 45.

Another embodiment is to provide the biologically active polypeptide having the amino acid sequence with SEQ ID NO: 4 and the functional derivatives thereof with, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19 with the N-terminal and C-terminal 6×His-tag sequence to aid in facile and efficient purification.

Another object is to provide a method for preparation of functional form of the polypeptide obtained by truncation of the upstream hydrophobic region SEQ ID NO: 4 which exhibits far greater activity and stability than the polypeptide with SEQ ID NO: 2.

Yet another object of the invention is to provide the method for preparation of cysteine variants which are obtained by site-directed mutagenesis of the non-conserved cysteine and other non-conserved amino acids in the polypeptides, SEQ ID NO: 4.

Yet another object of the invention is to provide a method for production of active polypeptide and its cysteine variants in pure and biologically active form.

Yet another object is to provide mutant cellulase polypeptides where cysteines are replaced by alanine or other suitable amino acid at positions corresponding to truncated polypeptide of cellulase with SEQ ID NO: 4. The positions may be Cys64, Cys89, Cys230 or Cys272 wherein the mutant polypeptides are also biologically active.

Yet another object is to provide mutant cellulase polypeptide where at least two cysteines are replaced by alanines or other suitable amino acid at different positions corresponding to native polypeptide of cellulase with SEQ ID NO: 4. The positions may be combinations of Cys64, Cys89, Cys230 or Cys272 wherein the mutant polypeptide are active and comparatively stable as the truncated sequence with SEQ ID NO: 4.

In another embodiment, the mutant cellulase polypeptide where at least three or all four cysteines are replaced by alanine or other suitable amino acid corresponding to positions Cys64, Cys89, Cys230 and Cys272 of truncated polypeptide of cellulase with SEQ ID NO: 4 wherein the mutant polypeptides are also active.

Yet another object is to provide a method for preparation of the polypeptide with the new Cellulose binding domain (CBD) sequence attached with a linker sequence to the polypeptide either at the N-terminal or at the C-terminal region in sequence with SEQ ID NO: 4.

TABLE 1

Description of Sequences

| SEQ ID NO. | Description |
|---|---|
| SEQ ID NO: 1 | Soil metagenome derived nucleotide sequence |
| SEQ ID NO: 2 | Polypeptide sequence of the cellulase derived from soil metagenome |
| SEQ ID NO: 3 | Sequence derived from soil metagenome, particularly nucleotide sequence of the gene after truncating the upstream hydrophobic patch |
| SEQ ID NO: 4 | Sequence derived from soil metagenome, particularly polypeptide sequence of the gene after truncating the upstream hydrophobic patch |

In another embodiments, any of the amino acids can be replaced with any other amino acid to produce more active and stable form of the polypeptide.

In another embodiments, additional amino acid residues can be added at any position by random or directed mutagenesis to obtain the active polypeptide.

As a preferred embodiment of this invention, the cellulase expressed by recombinant means can be reacted with a desired thiol reactive group agent under conditions that allow the attachment of the thiol reactive group like polyethylene glycol (PEG) to the native cysteines present in the cellulase to enhance its stability.

Consequently, in preferred embodiments of the invention, the functional polypeptide has the wide range of activity from 5-7.5 and having optimum activity at pH-6 and also exhibits high stability over wide range of pH, more specifically from pH 4-9 and is also less prone to aggregation.

The functional polypeptide in the preferred embodiment provides a cellulase which shows activity over a wide range of temperature from 30-70° C., optimum temperature of 58° C. and also very stable at high temperature retaining its activity for half of its maximum activity for almost 10 hours at 58° C.

In one aspect of the invention, the stability of the polypeptide is increased when incubated in the presence of 0.2% substrate CMC at 58° C.

In another aspect of the invention, the present polypeptide shows enhanced activity in the presence of ionic salts like NaCl, KCl, LiCl and the like salts.

In another aspect, the functional active polypeptide of the invention is a cellulase which is also highly stable in the presence of high concentration of ionic salts, more preferably 4N NaCl, 3M LiCl etc. The cellulase in the present invention retains 70%-100% activity on prolonged incubation for 30 days in such high salt concentrations.

Most of the cellulases require one or more mono or divalent cations for their activity. But the polypeptide of invention shows activity without the addition of cations and is not inhibited by the presence of EDTA. Further the activity shows enhancement in the presence of 1 mM $CoCl_2$, $FeSO_4$, $MnCl_2$.

The present invention discloses polypeptides and their functional derivatives which are active in the presence 0.25% of non-ionic detergents like Triton-X-100, Tween-20, Tween-80 and the like.

According to the preferred embodiments, the invention provides a functional polypeptides which have high specific activity towards various substrates containing 1,4-β- and 1,3-β-glucosidic linkages of polysaccharides as shown in Table 2.

TABLE 2

Substrate specificity of novel cellulase

| Substrate | Linkage type | Relative activity (%) |
|---|---|---|
| Na-CMC | β-1,4-glucan | 100% |
| Locust bean gum | α-1,6/, β-1,4-galatomannan | UD |
| Oat spelt xylan | β-1,4-xyloglucan | UD |
| Laminarin | β-1,3/1,6-glucan | UD |
| Barley beta glucan | β-1,3/1,4-glucan | 173% ± 5 |
| Avicel | β-1,4-glucan | UD |

The present invention provides a novel enzyme and its functional derivatives which are also active against the 1,4-β-linkage present in the chromogenic substrate, para-nitro phenol cellobioside.

The present invention also provides the functional derivatives of the functionally active polypeptide obtained by deletions or substitutions of one or more amino acids at different positions. These functional derivatives retain the characteristics cellulase activity. Such polypeptides can also be advantageous over the native polypeptide, for example increased pH optima and increased temperature stability, less aggregation propensity etc.

The polypeptides in the present invention can be fused to other polypeptide moieties attached with a linker peptide either at the N-terminal or at the C-terminal to further improve useful properties like high activity and functional and structural stability.

The functional polypeptide can be purified to homogeneity by using the combinations of different chromatography like ion exchange, affinity based chromatography, hydrophobic interaction chromatography, gel filtration etc. The functional polypeptide can also be fused to certain tags like 6x-His, HSV-tag, etc. to aid the purification process which can later be cleaved off if desired.

The invention also provides the recombinant vectors containing the nucleic acids of the invention encoding the functional polypeptide or functional derivatives thereof. The vectors may be *E. coli* based, yeast vector or any suitable eukaryotic or prokaryotic vectors.

The present invention also provides the recombinant hosts expressing the recombinant vectors with the nucleic acid encoding the various functional polypeptide or functional derivatives thereof. The host may be any bacteria, fungi, insect or mammalian cells.

The present invention provides a method for the production of functional polypeptides as well as functional derivatives thereof including a procedure for cultivating the hosts, and isolating the polypeptides by suitable methods so that high yield can be obtained.

General Methods Used in Examples

The cloning of novel cellulase gene was performed in the T7 promoter-based expression vector, pET-15(b) and *E. coli* strain was used as expression host, procured from Novagen Inc. (Madison, Wis.). DNA amplification and modifying enzymes such as Pfu DNA Polymerase, Restriction Endonucleases, T4 DNA ligase, DpnI were obtained from New England Biolabs (NEB, USA).

Phusion polymerase was procured from Thermo Scientific, USA. Oligonucleotides were synthesized from Integrated DNA technologies (IDT USA). The gel extraction of DNA as well as plasmid DNA isolation was done using the commercial kits and procedures suggested by manufacturers from Qiagen™. The soil DNA isolation was done by using UltraClean™ and PowerMax™ (Mo Bio Laboratories Inc., Carlsbad, Calif., USA). The library was constructed in vector pEZSeg™ (Lucigen corporation, Middleton, USA). Ni-NTA beads used to assist purification of protein carrying His-tag were from Qiagen. Automated DNA sequencing was done using ABI sequencer. Substrates for detecting cellulase activity like carboxymethyl cellulose (CMC), para-nitro phenol cellobioside (pNPC), barley-β-glucan, avicel, laminarin etc. were procured from Sigma-Aldrich (USA). All reagents used in the experiments were of highest quality grade available.

1. Recombinant DNA methods: In general, the methods and techniques used for recombinant DNA preparations are the same as most commonly used in the molecular biology with reference to text books like Sambrook, Molecular Cloning: A Laboratory Manual (Sambrook and Russell, 2001). However, in the context of present invention, the modifications are mentioned wherever they have been introduced in the examples section.

2. Zymography for detection of cellulase activity was carried out according to the protocol mentioned developed by Choi (Choi et al., 2009). 10% SDS gel was run to resolve the proteins based on their respective molecular weight. After electrophoresis, the gel was washed with 2.5% Triton-X to remove SDS for 30 minutes followed by thorough washing for 2-3 times with 50 mM Tris-Cl (pH-7.4). This procedure removes Triton-X-100 on incubation for half an hour. The gel was then overlaid on 0.5% agarose plate containing 0.5% CMC substrate and incubated for at least 2 hours at 37° C. Following incubation, the gel was removed and the plate was stained with the solution of 0.2% Congo red and followed by destaining with 1M NaCl. The active band was visualized as yellow zone of clearance on plate.

3. SDS-PAGE was run according to the protocol developed by Laemmli (Laemmli, 1970). Approximately 10 µg of Protein sample was mixed with 5× sample buffer (0.25M Tris-HCl, pH 6.8. 15% SDS. 50% glycerol. 25% β-mercaptoethanol. 0.01% bromophenol blue). The protein samples were denatured by boiling and centrifuged at 12,000 rpm for 5 minutes each. The discontinuous gel system was used having different concentration and pH of the resolving and stacking components. Resolving gel was casted in 1.5M Tris-Cl, pH-8.8 and different poly-acrylamide concentrations depending on the size of the protein.

4. The smaller sized protein requires high concentration of acrylamide and vice-versa. 5% stacking gel was prepared in 0.5M Tris-Cl, pH-6.8. Buffer tank was filled with 1×SDS running buffer and constant current of 20 mA was provided till the protein dye crosses stacking gel and current increased to 30 mA when the protein dye enters resolving gel. The gel was stained with Coomassie Brilliant Blue R250 dye solution (250 mg of dye in 4.5:4.5:1 mixture of methanol:water:glacial acetic acid) with gentle shaking and background absorbed dye was removed using destaining solution (30% methanol and 10% glacial acetic acid).

5. CMC Assay: The detection of reducing sugars was done using DNS (Di-nitro salicylic acid) assay. DNSA was prepared by dissolving 5 gm of dinitrosalicylic acid (1%) and 5 gm of NaOH (1%) in water. Then 19.2% Rochelle salt (Na-potassium tartrate) was added and dissolved. This was followed by addition of 0.05% Na-sulphite and 0.2% phenol. Lastly volume make up was done with water and then DNS reagent stored in amber colour bottles at 4° C. (Miller, 1959).

6. Glucose standard curve: Glucose monohydrate (1 mg/ml) was made in water and different volumes (upto 60 µl) were taken in 96-well PCR plates and 60 µl of DNS reagent was added (Xiao et al., 2005). All experiments were done in triplicates. The plate was covered with plastic mat and the reaction was subjected to heating at 95° C. for 5 minutes and then 100 µl of it was transferred to 96-well micro-plate and absorbance was taken at 540 nm (Miller, 1959). Reducing sugar concentration was calculated from a standard curve using the equation (y=mx+c).

7. Cellulase activity was measured in 60 µl reaction containing 30 µl of appropriately diluted enzyme and 30 µl of 2% CMC (dissolved in water). Care was taken so that the final concentration of sodium-citrate buffer (pH-6) remained 100 mM in reaction. The reaction was incubated at its optimum temperature for specified time and terminated with 60 µl of DNS reagent as explained above. Appropriate blanks were also included, one without enzyme (enzyme blank) and other without substrate (substrate blank).

EXAMPLES

The following examples are given by way of illustration of the present invention and therefore should not be construed to limit the scope of the present invention Example 1

Soil DNA Isolation and Library Preparation and Screening for Cellulases:

Soil DNA was isolated using commercially available kits (UltraClean™ and PowerMax™ kits) from Mo-Bio Laboratories Inc., Carlsbad, Calif., USA from IMTech (30.7478° N, 76.7337° E). 10 g of soil was taken in a sterile 50 ml tube followed by addition of 15 ml of bead solution and vortexing. The solution was then homogenized for 20 second followed by addition of 1.2 ml of solution 51 and 6 ml IRS solution (inhibitor removal solution) provided in the kit. Homogenization was repeated for 60 seconds and contents were transferred to 30 ml centrifuge tube and incubated at 70° C. for 1 hour. It was centrifuged for 10 minutes at maximum speed. Then 2 ml of solution S2 was added to supernatant, incubated at 4° C. for 20 min. Again centrifugation was performed at 10,000 rpm for 5 min and Supernatant was transferred to a clean centrifuged tube and 30 ml of solution S3 was added. The contents were mixed properly by inverting the tube twice. The sample was then loaded to spin filter and spun at 2500×g for 5 min. Flow through was discarded. Spin filter was washed 6 times with 70% ethanol. An additional empty spin was given to remove residual ethanol. spin filter was then placed into a new collection tube and 8 ml of solution S5 was added for elution and centrifuged at 2500×g for 10 min. In eluted sample 0.32 ml of 5 M NaCl and 16.6 ml cold Ethanol was added and Incubated over night at −20° C. The tubes were centrifuged at 10,000 rpm for 10 min and pellet was washed with 70% ethanol twice which was then dried and re-suspended in water or TE buffer. The DNA sample was run on the 0.8% agarose gel to see for the average size and to ascertain the grade of DNA isolated.

Isolated soil metagenomic DNA was partially digested with Sau3A1 and separated by Agarose gel Electrophoresis. The DNA fragments of 1-10 Kb were eluted from the gel using Qiagen Gel Extraction kit and the eluted fragment was End-Repaired. Blunt end cloning was performed using 2.5 µl of pEZseq vector (100 ng/µl) premix with 500 ng of genomic end repair DNA according to the pEZseq Blunt cloning kit recommendation. The ligation mixture was kept at 16° C. on water bath over night. Ligation mixture was transformed in electro competent *E. coli*. After transformation, mixture spread on LB ampicillin plate on which X-gal & IPTG were spread to select the recombinant clones. Recombinants show white colony while non-recombinant show blue colony (blue white screening or α-complementation). The clones obtained were screened on the LB plate containing 0.5% CMC (Sigma) as substrate. After overnight incubation, the plates were stained with 0.2% Congo Red (Sigma) for 15 minutes and destained with 1M NaCl (Teather and Wood, 1982). Plasmid was extracted from the clone harbouring the endoglucanase activity and the restriction digestion (EcoRI and HindIII, NEB) was done to see the size of the insert. The positive clone with cellulase activity had the insert size of 5-5.5 kb as seen by 0.8% Agarose gel electrophoresis Example 2

Amino Acid Sequence Analysis:

The positive clone from the library was sequenced by primer walking. The sequence was 5553 bp long. The clone showed the presence of 5-6 novel ORFs. The ORF encoding the cellulase gene in 1017 bp long was searched for sequence similarity and novelty was found by NCBI Blastp program. The ORF in the present invention, encoding cellulase comprised of 1017 base pairs and Blastp revealed identities=209/332 (65%), Positives=254/332 (76%) with cellulase of Paludibacter jiangxiensis. The ORF also encoded the upstream hydrophobic patch predicted by using SignalP 4.1 server (Petersen et al., 2011). The amino acid sequence was deduced using ExPASy translator software.

Example 3

Cloning of the Full Length ORF Encoding Cellulase Activity:

In order to clone and then express native like full length ORF encoding cellulase, the gene was PCR amplified using the pEZSeq vector harboring the unique gene fragment as a template. The PCR primers were designed so as to include unique restriction sites (BamHI and NdeI) in the gene for cloning into pET15(b) vector encoding N-terminal His-tag to assist in protein purification. The following PCR conditions were used for amplification of the gene in 100µl of reaction (50 ng of template DNA, 200 µM dNTP's mix, 10 µl of the standard 10× buffer, 0.5 µM of each primers Cel5R_F and Cel5R_R and 2.5U of pfu DNA polymerase. The following cycling parameters were used for amplification; initial denaturation at 95° C. for five minutes, final denaturation at 95° C. for 30 seconds, primer annealing at 55° C. for 1 minute, extension at 72° C. for 1 minute, a total number of 30 cycles and lastly final extension at 72° C. for 5 minute. The PCR amplified product was subjected to electrophoresis on 0.8% agarose gel and the single band corresponding to 1 Kb was obtained as expected.

```
                                              SEQ ID NO: 20
cel5R F  5' AATATACATATGAAGAAAAACTCAATCATTCTC 3'

SEQ ID NO: 21
cel5R R  5' AATATAGGATCCTCAGATATCCGGGTTTTCATC 3'
```

For cloning the amplified gene fragment in pET15(b), 500 ng of the vector and amplified product were digested with the NdeI and BamHI restriction enzymes in 50 µl reaction using the buffer NEB4 supplied by New England Biolabs, Inc., and incubating the reaction at 37° C. for 3 hours. The digested products were run on 0.8% agarose gel and were gel purified using the gel extraction kit from Qiagen™. The double digested insert and linearized vector were ligated in the molar ratio of 3:1 in 10 ul reaction using T4 DNA ligase enzyme supplied by New England Biolabs under standard ligation conditions at 16° C. for 12 hours. Following incubation, the enzyme was heat inactivated at 65° C. for 10 minutes. The ligation mix was transformed into XL1-blue competent cells and transformants obtained were picked and checked for the presence of gene of interest by Agarose Gel Electrophoresis. The DNA of the recombinant vector pER15b-Cel5R was transformed into the expression host BL21-DE3 to check for expression.

Expression Profile of Cellulase from *E. coli*:

The positive clone harboring the recombinant vector pET15b-Cel5R was grown in 10 ml of the Luria broth containing 100 µg/ml of ampicillin for overnight at 37° C. with shaking at 200 rpm. Then 1% of primary culture was inoculated in 50 ml of Luria Broth supplemented with 100 µg/ml of ampicillin and incubated with shaking at 200 rpm at 37° C. till the OD at 600 nm reached 0.6. 1 mM of IPTG was then added to the culture to induce the expression of the cellulase gene and the incubation continued again for another four hours. The cells were harvested by centrifugation at 6000 g and the supernatant was discarded. The cell pellet was resuspended in lysis buffer (20 mM phosphate buffer, pH 7.4, 300 mM NaCl, 1 mM PMSF, 10 mM imidazole) and sonicated for 30 minutes with 30 sec on and off cycle. The crude lysate was clarified by centrifugation at 18000 g for 30 min and pellet and supernatant were separated and loaded on 10% SDS poly-acrylamide gel to see the expression profile. The expression profile showed the presence of recombinant polypeptide in inclusion bodies as compared to non-induced cells. The inclusion bodies were purified and subjected to refolding by various refolding methods like On-column refolding by Ni-NTA beads, dialysis, dilution refolding, 96-well matrix refolding using different combinations of buffers.

Example 4

Recloning after Deletion of Hydrophobic Patch:

The gene sequence analysis by SignalP 4.1 prediction software showed the presence of upstream hydrophobic region with the cleavage site at amino acid residue 27. New primer to delete the upstream peptide region was synthesised (cel5R_Δ27_F) and the reverse primer (cel5R_R) was same as the previous one. The ORF was PCR amplified as explained above and cloned in pET15(b) vector between BamHI and NdeI sites with N-terminal 6×His-tag. The recombinant vector pET15(b) harboring the cellulase gene was transformed in *E. coli*. Rosetta (DE3) cells and the expression was checked on 10% SDS PAGE.

```
cel5R Δ27 F
                                              SEQ ID NO: 22
     5' AATATACATATGGAAAACAACAGGAAAACGGACTA 3'
```

Example 5

Overexpression, Refolding and Purification of Active Protein:

For protein purification, the cells were harvested and then lysed in sonication buffer (20 mM phosphate buffer, pH 7.4, 300 mM NaCl, 1 mM PMSF, 10 mM imidazole) with 30 sec on and off cycle for 30 min (Heat system, New York). The crude lysate was clarified by centrifugation at 18000 g for 30 min and the supernatant was loaded onto a pre-equilibrated Nickel-affinity column (GE Healthcare) at the flow rate of 1 ml/minute. The column washing was done using (20 mM phosphate buffer, pH 7.4, 300 mM NaCl, 30 mM imidazole) and enzyme was eluted with (20 mM phosphate buffer, pH 7.4, 300 mM NaCl, 300 mM imidazole). The eluted protein was dialysed in buffer containing 20 mM phosphate buffer pH 7.4, 10% glycerol and 300 mM NaCl with three times buffer exchange. The dialysed protein was concentrated, run on SDS-PAGE to see if there is aggregation and injected to Gel Filtration Chromatography on 120 ml Superdex-75, (GE Healthcare), pre equilibrated with 20 mM phosphate buffer pH 7.4 and 300 mM NaCl at the flow rate of 0.8 ml/minute. The peak fractions were collected and analyzed by 10% SDS poly-acrylamide gel. The purity of the protein was estimated by SDS-PAGE analysis and quantification was done by OD 280 nm using molar extinction coefficient for the polypeptide obtained from ExPASy protparam tool. On SDS-PAGE, a single band around 40 kDa was obtained. The protein remained undegraded during the entire procedure.

Example 6

Construction of Cysteine Mutants and their Bioactivity:

Single site cysteine to alanine mutations were performed using high fidelity Phusion polymerase Kit™ (Thermo scientific). Complementary Primers with the desired mutations in the middle were designed and extended by phusion polymerase in the temperature cycler. The list of primers used for mutagenesis is shown in Table 3 from SEQ ID NO: 23 to SEQ ID NO: 30. The 25 µl PCR reaction included 50 ng of template DNA, 200 µM dNTPs mix, 2.5 µl of the standard 10× buffer, 0.504 of each primers, 2U of phusion polymerase enzyme (Thermo scientific).

TABLE 3

List of primers used in the study

| SEQ ID NO: | PRIMER NAME | PRIMER SEQUENCE (5'-3') |
|---|---|---|
| SEQ ID NO: 20 | cel5R F | AATATACATATGAAGAAAAACTCAATCATTCTC |
| SEQ ID NO: 21 | cel5R R | AATATAGGATCCTCAGATATCCGGGTTTTCATC |

TABLE 3-continued

List of primers used in the study

| SEQ ID NO: | PRIMER NAME | PRIMER SEQUENCE (5'-3') |
|---|---|---|
| SEQ ID NO: 22 | cel5R α27 F | AATATACATATGGAAAACAACAGGAAAACGGACTA |
| SEQ ID NO: 23 | C64A F | CGATTGGAAAGCGACGGTCGTCAG |
| SEQ ID NO: 24 | C64A R | CTGACGACCGTCGCTTTCCAATCG |
| SEQ ID NO: 25 | C89A F | GAATTTGCCTTACAGGCGATCACCCCTG |
| SEQ ID NO: 26 | C89A R | CAGGGGTGATCGCCTGTAAGGCAAATTC |
| SEQ ID NO: 27 | C230A F | CGTATCGGAGGCGGGCGGCTC |
| SEQ ID NO: 28 | C230A R | GAGCCGCCCGCCTCCGATACG |
| SEQ ID NO: 29 | C272A F | GAACGAAACCGCGTCCATGCTGCTC |
| SEQ ID NO: 30 | C272A R | GAGCAGCATGGACGCGGTTTCGTTC |

The following cycling parameters were used for amplification; initial denaturation at 98° C. for five minutes, final denaturation at 98° C. for 30 seconds, primer annealing at 55° C. for 30 seconds, extention at 72° C. for 3.5 minute, a total number of 20 cycles and lastly final extention at 72° C. for 5 minute. Then 5 μl of PCR amplified product was subjected to electrophoresis on 0.8% agarose gel to see the amplification at the expected size. The remaining PCR product was digested with DpnI (NEB) enzyme using 20U of enzyme in the PCR reaction and incubating at 37° C. for one hour to remove the methylated template DNA. The DpnI digested DNA was transformed in XL1B cells. The transformants obtained were picked and plasmid DNA isolated. The confirmation of the mutated DNA was done by sequencing. After sequencing confirmation, the cloned plasmids transformed in Rosetta (BL21) cells. Table 4 and Table 5 show the list of mutants along with specific mutations at different positions along with their protein sequence with SEQ ID NO: 5 to SEQ ID NO: 19 and nucleotide sequence with SEQ ID NO: 31 to SEQ ID NO: 45 respectively. The polypeptides were purified by the same method as explained above.

TABLE 4

Cysteine to Alanine substitution(s) on truncated cellulase polypeptide sequence (SEQ ID NO: 4, 1-311)

| Molecule | Modification |
|---|---|
| SEQ ID NO: 5 | Cys 64 Ala |
| SEQ ID NO: 6 | Cys 89 Ala |
| SEQ ID NO: 7 | Cys 230 Ala |
| SEQ ID NO: 8 | Cys 272 Ala |
| SEQ ID NO: 9 | Cys 64 Ala, Cys 89 Ala |
| SEQ ID NO: 10 | Cys 64 Ala, Cys 230 Ala |
| SEQ ID NO: 11 | Cys 64 Ala, Cys 272 Ala |
| SEQ ID NO: 12 | Cys 89 Ala, Cys 230 Ala |
| SEQ ID NO: 13 | Cys 89 Ala, Cys 272 Ala |
| SEQ ID NO: 14 | Cys 230 Ala, Cys 272 Ala |
| SEQ ID NO: 15 | Cys 64 Ala, Cys 89 Ala, Cys 230 Ala |
| SEQ ID NO: 16 | Cys 64 Ala, Cys 230 Ala, Cys 272 Ala |
| SEQ ID NO: 17 | Cys 89 Ala, Cys 230 Ala, Cys 272 Ala |
| SEQ ID NO: 18 | Cys 64 Ala, Cys 89 Ala, Cys 272 Ala |
| SEQ ID NO: 19 | Cys 64 Ala, Cys 89 Ala Cys 230 Ala, Cys 272 Ala |

TABLE 5

Cysteine to Alanine substitution(s) on truncated cellulase nucleotide sequence (SEQ ID NO: 3 1-936)

| Molecule | Modification |
|---|---|
| SEQ ID NO: 31 | Codon for cysteine at position 190 is replaced by alanine |
| SEQ ID NO: 32 | Codon for cysteine at position 265 is replaced by alanine |
| SEQ ID NO: 33 | Codon for cysteine at position 688 is replaced by alanine |
| SEQ ID NO: 34 | Codon for cysteine at position 814 is replaced by alanine |
| SEQ ID NO: 35 | Codon for cysteine at positions 190 and 265 are replaced by alanine |
| SEQ ID NO: 36 | Codon for cysteine at positions 190 and 688 are replaced by alanine |
| SEQ ID NO: 37 | Codon for cysteine at positions 190 and 814 are replaced by alanine |
| SEQ ID NO: 38 | Codon for cysteine at positions 265 and 688 are replaced by alanine |
| SEQ ID NO: 39 | Codon for cysteine at positions 265 and 814 are replaced by alanine |
| SEQ ID NO: 40 | Codon for cysteine at positions 688 and 814 are replaced by alanine |
| SEQ ID NO: 41 | Codon for cysteine at positions 190, 265 and 688 are replaced by alanine |
| SEQ ID NO: 42 | Codon for cysteine at positions 190, 688 and 814 are replaced by alanine |
| SEQ ID NO: 43 | Codon for cysteine at positions 265, 688 and 814 are replaced by alanine |
| SEQ ID NO: 44 | Codon for cysteine at positions 190, 265 and 814 are replaced by alanine |
| SEQ ID NO: 45 | Codon for cysteine at positions 190, 265, 688 and 814 are replaced by alanine |

Relative activity and melting temperature of various cysteines to alanine mutants of SEQ ID NO: 4. are provided in Table 6. The activities and melting temperatures of most of the mutants were lower than SEQ ID NO: 4 except SEQ ID NO: 8.

TABLE 6

Relative activity and melting temperature of various cysteines to alanine mutants of SEQ ID NO: 4.

| Mutant | Relative activity (%) | Melting temp. (° C.) |
| --- | --- | --- |
| SEQ ID NO: 4 | 100 ± 1.836 | 65.99 |
| SEQ ID NO: 5 | 87.85 ± 1.17 | 65.1 |
| SEQ ID NO: 6 | 78.96 ± 5.322 | 63.5 |
| SEQ ID NO: 7 | 74.46 ± 3.02 | 64.5 |
| SEQ ID NO: 8 | 106.91 ± 3.4 | 67.1 |
| SEQ ID NO: 9 | 73.63 ± 1.73 | 60.7 |
| SEQ ID NO: 10 | 72.94 ± 1.86 | 63.8 |
| SEQ ID NO: 11 | 109.71 ± 0.53 | 65.4 |
| SEQ ID NO: 12 | 61.46 ± 3.87 | 61.4 |
| SEQ ID NO: 13 | 62.93 ± 2.62 | 63.5 |
| SEQ ID NO: 14 | 70.92 ± 1.04 | 64.4 |
| SEQ ID NO: 19 | 19.24 ± 1.78 | 55 |

Example 7

Enzyme Characterization and Cellulase Activity

The activity of the enzyme was checked by 3,5-dinitrosalicylic acid (Sigma) assay (Miller, 1959) which measures the reducing sugars produced by hydrolysis of polysaccharide. One unit (U) is defined as the quantity of enzyme required to release 1 μmol of reducing sugar per min. The optimal pH was determined in 100 mM of different buffers (pH 3-10) containing 1% (w/v) CMC for 15 min. The buffers used were Na-citrate (pH-3-6), Tris-Cl (pH 7-8) and glycine/NaOH (pH 9-10). For determining optimal temperature, the reaction was performed in the optimal buffer pH at temperature varying from 30-70° C. for 15 minutes. The thermo stability was determined by measuring the residual activity after incubation at various temperatures (4° C., 25° C., 50° C., 55° C., 58° C., 60° C.) for various time intervals. The thermal stability in the presence of substrate (0.2% CMC) was also checked at 58° C. The pH stability was checked by incubating enzyme in 100 mM of different buffer at 25° C. and then checking the residual activity after different time intervals under optimal conditions. Zymography was carried according to the protocol described (Choi et al., 2009).

The substrate specificity was checked by using 1% of different substrates (avicel, barley-β-glucan, locust bean gum, laminarin, Xylan, Na-CMC, avicel) under standard assay conditions. The activity on pNPC and pNPG (sigma) was checked by incubating 50 μl of 10 mM substrate with 50 μl of diluted enzyme for 15 minutes at 58° C. and stopping the reaction with 100 μl of 1M $Na_2CO_3$ and the absorbance at 405 nm was taken. One unit is defined as the quantity of enzyme required to release 1 μmole of para-nitro phenol per minute. The effect of various metal ions was checked at 1 mM concentration. The effect of organic solvents and detergents were tested at 5% and 0.25% concentration respectively.

Example 8

Halotolerance and Salt Activation

Salt activation was checked by checking the activity in the presence of 1M-3M NaCl, LiCl and KCl. Halotolerance was checked by incubating the enzyme in the presence of salts for various intervals of time and then checking the residual activity.

Advantages of the Invention

1. The novel endoglucanase, belong to GH5 family, identified by soil metagenomic approach is tolerant to high salt conditions, temperature and pH.
2. The novel endoglucanase shows thermostability up to 58° C. and pH stability between 5-9.
3. This endoglucanase shows halotolerance and extreme halostability in 4M NaCl, 3M LiCl and 2M KCl which is higher than other known halostable cellulases.
4. The combination of extreme halostability with moderate thermal and pH stability makes it a potential candidate for industrial applications.

REFERENCES

1. Aubert, J.-P., Béguin, P., and Millet, J. (1988). Biochemistry and genetics of cellulose degradation (Academic Press).
2. Bhat, M. (2000). Cellulases and related enzymes in biotechnology. Biotechnology advances 18, 355-383.
3. Choi, N.-S., Kim, B.-H., Park, C.-S., Han, Y. J., Lee, H. W., Choi, J. H., Lee, S.-G., and Song, J. J. (2009). Multiple-layer substrate zymography for detection of several enzymes in a single sodium dodecyl sulfate gel. Analytical biochemistry 386, 121-122.
4. Daniel, R. (2005). The metagenomics of soil. Nat Rev Microbiol 3, 470-478.
5. Ferrer, M., Golyshin, P., Golyshina, O., Chernikova, T., Strompl, C., Timmis, K., Elborough, K., and Jarvis, G. (2008). Cellulases from Rumen (Google Patents).
6. Handelsman, J. (2004). Metagenomics: application of genomics to uncultured microorganisms. Microbiol Mol Biol Rev 68, 669-685.
7. Kanokratana, P., Eurwilaichitr, L., Pootanakit, K., and Champreda, V. (2014). Identification of glycosyl hydrolases from a metagenomic library of microflora in sugarcane bagasse collection site and their cooperative action on cellulose degradation. Journal of bioscience and bioengineering.
8. Ko, K.-C., Lee, J. H., Han, Y., Choi, J. H., and Song, J. J. (2013). A novel multifunctional cellulolytic enzyme screened from metagenomic resources representing ruminal bacteria. Biochemical and biophysical research communications 441, 567-572.
9. Laemmli, U.K. (1970). Cleavage of structural proteins during the assembly of the head of bacteriophage T4. Nature 227, 680-685.
10. Lombard, V., Golaconda Ramulu, H., Drula, E., Coutinho, P. M., and Henrissat, B. (2014). The carbohydrate-active enzymes database (CAZy) in 2013. Nucleic Acids Res 42, D490-495.
11. Lynd, L. R., Weimer, P. J., Van Zyl, W. H., and Pretorius, I. S. (2002). Microbial cellulose utilization: fundamentals and biotechnology. Microbiology and molecular biology reviews 66, 506-577.
12. Miller, G. L. (1959). Use of dinitrosalicylic acid reagent for determination of reducing sugar. Analytical chemistry 31, 426-428.
13. Okano, H., Ozaki, M., Kanaya, E., Kim, J. J., Angkawidjaja, C., Koga, Y., and Kanaya, S. (2014). Structure and stability of metagenome-derived glycoside hydrolase family 12 cellulase (LC-CelA) a homolog of Cel12A from *Rhodothermus marinus*. FEBS Open Bio 4, 936-946.
14. Petersen, T. N., Brunak, S., von Heijne, G., and Nielsen, H. (2011). SignalP 4.0: discriminating signal peptides from transmembrane regions. Nat Methods 8, 785-786.
15. Sambrook, J., and Russell, D. W. (2001). Molecular Cloning: A Laboratory Manual (Cold Spring Harbor Laboratory Press).
16. Teather, R. M., and Wood, P. J. (1982). Use of Congo red-polysaccharide interactions in enumeration and characterization of cellulolytic bacteria from the bovine rumen. Appl Environ Microbiol 43, 777-780.

17. Xiao, Z., Storms, R., and Tsang, A. (2005). Microplate-based carboxymethylcellulose assay for endoglucanase activity. Anal Biochem 342, 176-178.
18. Xing, M.-N., Zhang, X.-Z., and Huang, H. (2012). Application of metagenomic techniques in mining enzymes from microbial communities for biofuel synthesis. Biotechnology advances 30, 920-929.
19. Zengler, K., Toledo, G., Rappe, M., Elkins, J., Mathur, E. J., Short, J. M., and Keller, M. (2002). Cultivating the uncultured. Proc Natl Acad Sci USA 99, 15681-15686.

We claim:

1. An isolated metagenome derived nucleotide sequence consisting of the polynucleotide sequence SEQ ID NO: 3, wherein the metagenome derived nucleotide sequence encodes a polypeptide having cellulase activity.

2. An isolated polypeptide encoded by the metagenome derived nucleotide sequence as claimed in claim 1, wherein the polypeptide has the amino acid sequence SEQ ID NO: 4.

3. A recombinant vector comprising the metagenome derived nucleotide sequence as claimed in claim 1, wherein the recombinant vector is selected from the group consisting of an E. coli expression vector, a yeast expression vector, a filamentous fungal expression vector, an insect expression vector, and an animal expression vector.

4. The polypeptide as claimed in claim 2, wherein the polypeptide has high specific activity towards µ-1, 4 linkages in substrates selected from the group consisting of Carboxy-methyl cellulose and Barley-µ-glucan.

5. An expression vector comprising the polynucleotide sequence of SEQ ID NO: 3 which encodes a polypeptide having cellulase activity, wherein the expression vector is selected from the group consisting of an E. coli expression vector, a yeast expression vector, a filamentous fungal expression vector, an insect expression vector, and an animal expression vector.

6. An expression vector comprising the polynucleotide sequence of SEQ ID NO: 3 which encodes a polypeptide having amino acid sequence of SEQ ID NO: 4, and wherein the polypeptide has cellulase activity, wherein the expression vector is selected from the group consisting of an E. coli expression vector, a yeast expression vector, a filamentous fungal expression vector, an insect expression vector, and an animal expression vector.

7. A host cell expressing the recombinant vector as claimed in claim 3, wherein the host cell is selected from the group consisting of E. coli, a yeast cell, Bacillus subtilis, Aspergillus niger, an insect cell, and an animal cell.

* * * * *